United States Patent
Wakamatsu

(10) Patent No.: US 10,441,532 B2
(45) Date of Patent: Oct. 15, 2019

(54) METHOD OF PRODUCING TRANSDERMAL ABSORPTION SHEET

(71) Applicant: FUJIFILM Corporation, Tokyo (JP)

(72) Inventor: Satoshi Wakamatsu, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 217 days.

(21) Appl. No.: 15/600,797

(22) Filed: May 22, 2017

(65) Prior Publication Data

US 2017/0333342 A1 Nov. 23, 2017

(30) Foreign Application Priority Data

May 23, 2016 (JP) ................... 2016-102496

(51) Int. Cl.
| | | |
|---|---|---|
| *A61M 37/00* | (2006.01) | |
| *A61K 9/00* | (2006.01) | |
| *B29C 39/24* | (2006.01) | |
| *A61K 47/36* | (2006.01) | |
| *A61K 47/38* | (2006.01) | |

(Continued)

(52) U.S. Cl.
CPC ............ *A61K 9/0021* (2013.01); *A61K 47/36* (2013.01); *A61K 47/38* (2013.01); *A61M 37/0015* (2013.01); *B29C 39/24* (2013.01); *A61K 9/7007* (2013.01); *A61M 2037/0053* (2013.01); *B29D 7/01* (2013.01); *B29L 2031/7544* (2013.01)

(58) Field of Classification Search
CPC .. A61M 2037/0053; A61M 2037/0061; B29D 7/00–01; B81C 1/00111
See application file for complete search history.

(56) References Cited

U.S. PATENT DOCUMENTS

| | | | | |
|---|---|---|---|---|
| 2008/0269685 A1* | 10/2008 | Singh | ................... | A61K 9/0021 604/173 |
| 2013/0292868 A1* | 11/2013 | Singh | ................... | A61K 9/0021 264/102 |
| 2015/0238743 A1* | 8/2015 | Che | ....................... | B32B 37/025 156/285 |

FOREIGN PATENT DOCUMENTS

| | | |
|---|---|---|
| EP | 2921201 | 9/2015 |
| EP | 3144030 | 3/2017 |

(Continued)

OTHER PUBLICATIONS

"Search Report of European Counterpart Application," dated Sep. 25, 2017, p. 1-p. 9.

(Continued)

*Primary Examiner* — William P Bell
*Assistant Examiner* — Andrew L Swanson
(74) *Attorney, Agent, or Firm* — JCIPRNET

(57) ABSTRACT

A method of producing a transdermal absorption sheet includes: filling needle-like recessed portions on a mold having the needle-like recessed portions with a polymer solution; drying the filled polymer solution to form a polymer layer; and peeling off the polymer layer, wherein, in drying the polymer solution, low rate drying conditions are set in a concentration range in which an average solid content concentration of the polymer solution is 70 wt % to 80 wt %. When a constant drying rate of water is used as an index, in the concentration range in which the average solid content concentration of the polymer solution is 70 wt % to 80 wt %, and the constant drying rate is lower than a maximum value of a constant drying rate under a drying condition where the average solid content concentration of the polymer solution is less than 70 wt % and more than 80 wt %.

9 Claims, 14 Drawing Sheets

(51) Int. Cl.
  *B29D 7/01* (2006.01)
  *B29L 31/00* (2006.01)
  *A61K 9/70* (2006.01)

(56) References Cited

FOREIGN PATENT DOCUMENTS

| | | | |
|---|---|---|---|
| JP | 2008245955 | 10/2008 | |
| JP | 2011245055 | 12/2011 | |
| JP | 2015217043 | 12/2015 | |
| WO | WO-2014077243 A1 * | 5/2014 | ........... B32B 37/025 |

OTHER PUBLICATIONS

"Office Action of Japan Counterpart Application," dated Jul. 4, 2019, with English translation thereof, pp. 1-4.
"Office Action of Japan Counterpart Application", dated Apr. 22, 2019, with English translation thereof, p. 1-p. 7.

* cited by examiner

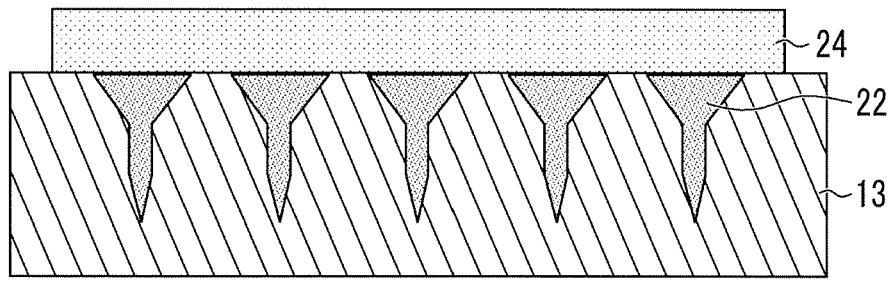
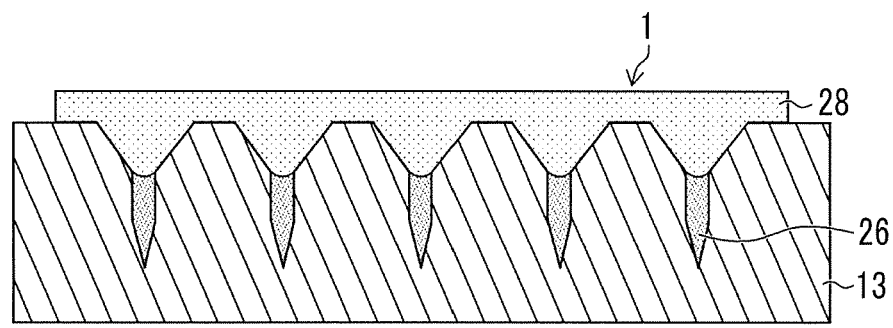
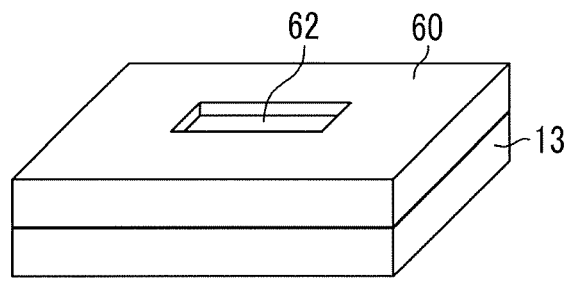
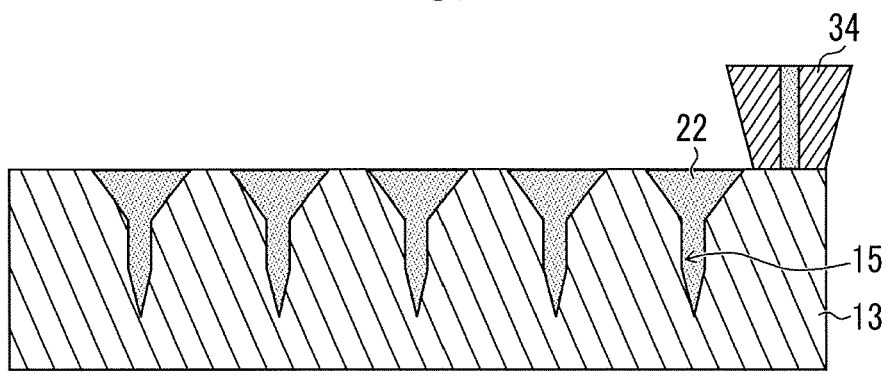

METHOD OF PRODUCING TRANSDERMAL ABSORPTION SHEET

CROSS-REFERENCE TO RELATED APPLICATIONS

The present application claims priority under 35 U.S.C. § 119 to Japanese Patent Application No. 2016-102496, filed on May 23, 2016. The above application is hereby expressly incorporated by reference, in its entirety, into the present application.

BACKGROUND OF THE INVENTION

1. Field of the Invention

The present invention relates to a method of producing a transdermal absorption sheet and particularly to a method of producing a transdermal absorption sheet by shape transfer using a mold having needle-like recessed portions formed thereon.

2. Description of the Related Art

As a method for administering a drug or the like through a living body surface, that is, a skin, a mucous membrane, or the like, a drug injection method of using a transdermal absorption sheet on which needle-like protruding portions having a high aspect ratio and containing a drug (hereinafter, also referred to as "microneedles") are formed and inserting the needle-like protruding portions into a skin is used.

As a method of producing such a transdermal absorption sheet, for example, JP2008-245955A discloses a method of producing a transdermal absorption sheet including injecting a solution of a resin polymer into recessed portion array on a stamper on which a recessed portion array, which is an inverted shape of a protruding portion array, is formed to form a protruding portion array with the solution of the resin polymer, then drying and curing the resin polymer to form an aggregate of the resin polymer, and peeling off the aggregate of the resin polymer from the stamper.

SUMMARY OF THE INVENTION

As disclosed in JP2008-245955A, in the production of a transdermal absorption sheet using a mold having needle-like recessed portions, in the step of drying the polymer solution, a solvent (moisture) is volatilized from the surface side of the polymer layer (the side opposite to the mold) by drying. Accordingly, the surface side of the polymer layer loses its fluidity and the polymer solution in the needle-like recessed portions is in a sealed state. Further, when drying proceeds, vapor formed by drying of the polymer solution in the needle-like recessed portions is diffused to the outside and the pressure inside the needle-like recessed portions is reduced by drying shrinkage. In the case in which the mold is soft or a through-hole is provided in the mold, the internal pressure can be relaxed and thus needle-like protruding portions can be formed in a good shape. However, in the case in which the shape of the mold is not changed or a through-hole is not provided in the mold, bubbles constituted of a polymer solution dissolved gas and water vapor are generated in the needle-like recessed portions to relax the pressure inside the needle-like recessed portions. Due to the generated bubbles, the polymer solution in the needle-like recessed portions is deformed and an inverted shape of the needle-like recessed portion cannot be formed so that the shape of the needle-like protruding portion of the transdermal absorption sheet becomes poor.

In addition, depending on the drying conditions, wrinkles are formed on the surface of the polymer layer.

The present invention has been made under the consideration of such circumstances and an object of the present invention is to provide a method of producing a transdermal absorption sheet in which formation of wrinkles on the surface of a polymer layer (the back surface of the transdermal absorption sheet) is suppressed and the shape of the needle-like protruding portion of the transdermal absorption sheet is good.

In order to achieve the above object, the present invention provides a method of producing a transdermal absorption sheet comprising, in this order: a polymer solution filling step of filling needle-like recessed portions on a mold having the needle-like recessed portions arranged two-dimensionally with a polymer solution; a polymer solution drying step of drying the polymer solution filling the needle-like recessed portions to form a polymer layer; and a peeling-off step of peeling off the polymer layer from the mold, in which in the polymer solution drying step, low rate drying conditions are set in a concentration range in which an average solid content concentration of the polymer solution is 70 wt % or more and 80 wt % or less in terms of weight percent, and when a constant drying rate of water is used as an index, in the concentration range in which the average solid content concentration of the polymer solution is 70 wt % or more and 80 wt % or less in terms of weight percent, the constant drying rate is set to be lower than a maximum value of a constant drying rate under drying conditions in a concentration range in which the average solid content concentration of the polymer solution is less than 70 wt % and more than 80 wt % in terms of weight percent.

The present inventors have found that in the polymer solution drying step, the polymer solution is dried and in the concentration range in which the average solid content concentration in the polymer solution is 70 wt % or more and 80 wt % or less in terms of weight percent, the fluidity of the polymer solution filling the needle-like recessed portions is reduced and solidified. According to the present invention, a concentration gradient of the polymer solution in a film thickness direction can be reduced by setting the drying conditions in the concentration range in which the average solid content concentration is 70 wt % or more and 80 wt % or less as low rate drying conditions. Accordingly, it is possible to suppress a rapid shape deformation of the polymer solution in the needle-like recessed portions of the mold and to stabilize the shape of the needle-like protruding portion of a transdermal absorption sheet to be produced.

In addition, when the constant drying rate in the concentration range in which the average solid content concentration in the polymer solution is 70 wt % or more and 80 wt % or less is set to be lower than a maximum value of the constant drying rate in the concentration range in which the average solid content concentration is less than 70 wt % and more than 80 wt %, that is, the constant drying rate in the concentration range in which the average solid content concentration is less than 70 wt % and more than 80 wt % is increased, it is possible to shorten the drying time.

Since drying proceeds from the surface side of the polymer solution, even in the range in which the average solid content concentration of the polymer solution is less than 70 wt %, the fluidity of the polymer solution is reduced and wrinkles may be formed on the surface of the polymer layer in some cases. By decreasing the constant drying rate in the concentration range in which the average solid content concentration is 70 wt % or more and 80 wt % or less, it is possible to reduce the formed wrinkles and suppress formation of wrinkles.

Accordingly, it is possible to produce a transdermal absorption sheet in which needle-like protruding portions are formed by stabilizing and transferring the shape of the needle-like recessed portion of the mold and formation of wrinkles is suppressed.

In the present invention, the term "low rate drying conditions" refers to conditions for slowly performing drying not to form wrinkles and cause defects in the shape of the needle-like protruding portion when predetermined drying conditions are set, and drying is performed by appropriately setting humidity and temperature, wind speed, atmospheric pressure, and the like according to the type of the polymer solution. In addition, regarding the solid content concentration of the polymer layer, since the solid content concentration varies in the thickness direction and the in-plane direction to form a concentration distribution, the term "average solid content concentration" is used as an average solid content concentration of the entirety of the polymer layer.

According to another aspect of the present invention, it is preferable that the constant drying rate of water under the drying conditions in the concentration range in which the average solid content concentration of the polymer solution is 70 wt % or more and 80 wt % or less in terms of weight percent is 0.10 kg/(h·m$^2$) or less.

In the aspect, the drying conditions in the range in which the average solid content concentration is 70 wt % or more and 80 wt % or less are defined and it is possible to sufficiently decrease the drying rate when the constant drying rate of water in the average solid content concentration is set to 0.10 kg/(h·m$^2$) or less.

In another aspect of the present invention, it is preferable that in the concentration range in which the average solid content concentration of the polymer solution is 70 wt % and more and 80 wt % or less in terms of weight percent, a lid having an opening portion is placed at a position where the lid covers the polymer solution.

According to the aspect, when the lid is placed in the concentration range in which the average solid content concentration is 70 wt % or more and 80 wt % or less, the inside of the lid is in an almost windless state and the relative humidity inside the lid is increased, thereby decreasing the constant drying rate.

In another aspect of the present invention, it is preferable that the method further comprises a drug solution filling step of filling the needle-like recessed portions with a drug-containing solution before the polymer solution filling step.

According to the aspect, the drug can be concentrated at the tip ends of the needle-like protruding portions by filling the needle-like recessed portions with the drug-containing solution in advance. Accordingly, it is possible to reduce the amount of an expensive drug and the production cost.

In another aspect of the present invention, it is preferable that the method further comprises a drug solution drying step of drying the drug-containing solution after the drug solution filling step before the polymer solution filling step.

According to the aspect, when the drug-containing solution is dried after the filling of the drug-containing solution, it is possible to stabilize the shape of the tip end of the needle-like protruding portion including the drug.

In another aspect of the present invention, it is preferable that the polymer solution contains a drug.

According to the aspect, it is possible to perform application using one solution and simplify the production step when a drug is incorporated into the polymer solution.

In another aspect of the present invention, it is preferable that the constant drying rate in at least part of the concentration range in which the average solid content concentration of the polymer solution is less than 70 wt % in terms of weight percent is set to be higher than the constant drying rate in the concentration range in which the average solid content concentration of the polymer solution is 70 wt % or more and 80 wt % or less in terms of weight percent.

According to the aspect, when the constant drying rate under the drying conditions in at least part of the concentration range in which the average solid content concentration is less than 70 wt % is increased, it is possible to shorten the time for the entire polymer solution drying step. In addition, when drying is performed under the drying condition in which the constant drying rate is high in the concentration range in which the average solid content concentration is less than 70 wt %, there is a concern of wrinkles being formed on the surface of the polymer layer due to rapid drying. When the drying condition in the concentration range in which the average solid content concentration is 70 wt % or more and 80 wt % or less is set as a condition in which the constant drying rate is low, the formed wrinkles are reduced and thus the formed wrinkles can be removed.

In another aspect of the present invention, it is preferable that the constant drying rate in at least part of the concentration range in which the average solid content concentration of the polymer solution is more than 80 wt % in terms of weight percent is set to be higher than the constant drying rate in the concentration range in which the average solid content concentration of the polymer solution is 70 wt % or more and 80 wt % or less in terms of weight percent.

According to the aspect, when the constant drying rate under the drying conditions in at least part of the concentration range in which the average solid content concentration is more than 80 wt % is increased, it is possible to shorten the time for the entire polymer solution drying step.

In another aspect of the present invention, it is preferable that a polymer contained in the polymer solution includes at least one of sodium chondroitin sulfate, hydroxypropyl cellulose, or dextran.

In the aspect, a preferable specific example of the polymer contained in the polymer solution is defined. Since the polymer has biocompatibility, it is possible to suitably use the polymer as a material for the transdermal absorption sheet.

In another aspect of the present invention, it is preferable that a sheet portion average thickness after the polymer solution drying step is 50 µm or more and 500 µm or less.

In the aspect, the sheet portion average thickness of the produced transdermal absorption sheet is defined. When the sheet portion average thickness is thick, the concentration range in which the polymer solution in the needle-like recessed portions is dried and the fluidity is reduced is increased. When the drying rate in the concentration range in which the average solid content concentration is 70 wt % or more and 80 wt % or less is decreased by producing the transdermal absorption sheet in such a solid content amount that the sheet portion average thickness after the drying step is set to be in the above range, it is possible to produce a transdermal absorption sheet in which formation of wrinkles is suppressed and the shape of the needle-like protruding portion is good.

In the present invention, the term "sheet portion average thickness" refers to an average thickness of the whole region excluding the needle-like protruding portions in the produced transdermal absorption sheet.

According to the method of producing a transdermal absorption sheet of the present invention, when the constant drying rate of water is used as an index, the constant drying rate under the drying conditions in the range in which the solid content concentration in the polymer solution is 70 wt % or more and 80 wt % or less is set to be lower than the maximum value of the constant drying rate under the drying conditions in the range in which the average solid content concentration is less than 70 wt % and more than 80 wt %, it is possible to suppress a rapid variation in pressure inside the needle-like recessed portions. Accordingly, it is possible to stabilize the shape of the needle-like protruding portion of a transdermal absorption sheet to be produced.

In addition, when the drying rate in the range in which the solid content concentration is 70 wt % or more and 80 wt % or less is decreased even in the case in which wrinkles are formed in the surface the polymer layer at drying at a solid content concentration of less than 70 wt %, it is possible to reduce the formed wrinkles and suppress formation of wrinkles. Accordingly, it is possible to produce a transdermal absorption sheet in which wrinkles are not formed on the back surface side of the transdermal absorption sheet and the shape of the needle-like protruding portion is good.

BRIEF DESCRIPTION OF THE DRAWINGS

FIG. 21 is a diagram illustrating the step of forming the polymer sheet.

FIG. 22 is a diagram illustrating the step of forming the polymer sheet.

FIG. 23 is a view in which a lid is placed on the mold.

FIG. 24 is a diagram illustrating another step of forming a polymer sheet.

DESCRIPTION OF THE PREFERRED EMBODIMENTS

Hereinafter, a method of producing a transdermal absorption sheet of the present invention will be described with reference to the attached drawings. Incidentally, in the specification, numerical values indicated using the expression "to" mean a range including the numerical values indicated before and after the expression "to" as the lower limit and the upper limit.

(Transdermal Absorption Sheet)

Figure 1:
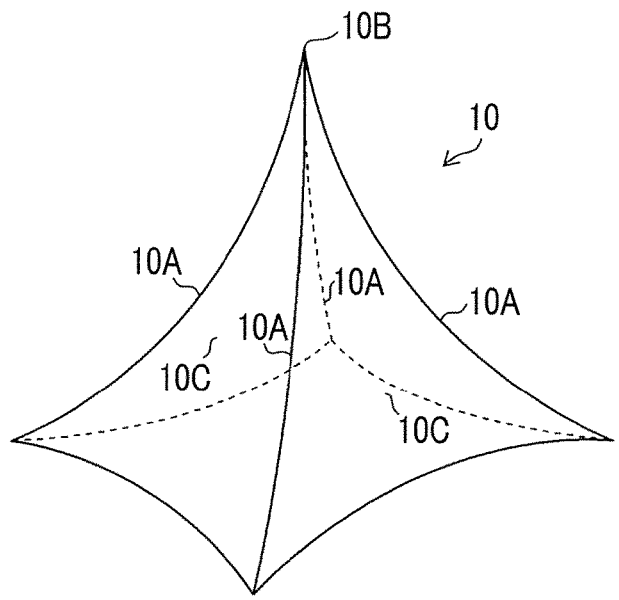
FIG. 1 is a perspective view showing a pyramidal microneedle (needle-like protruding portion) of a transdermal absorption sheet.
Figure 2:
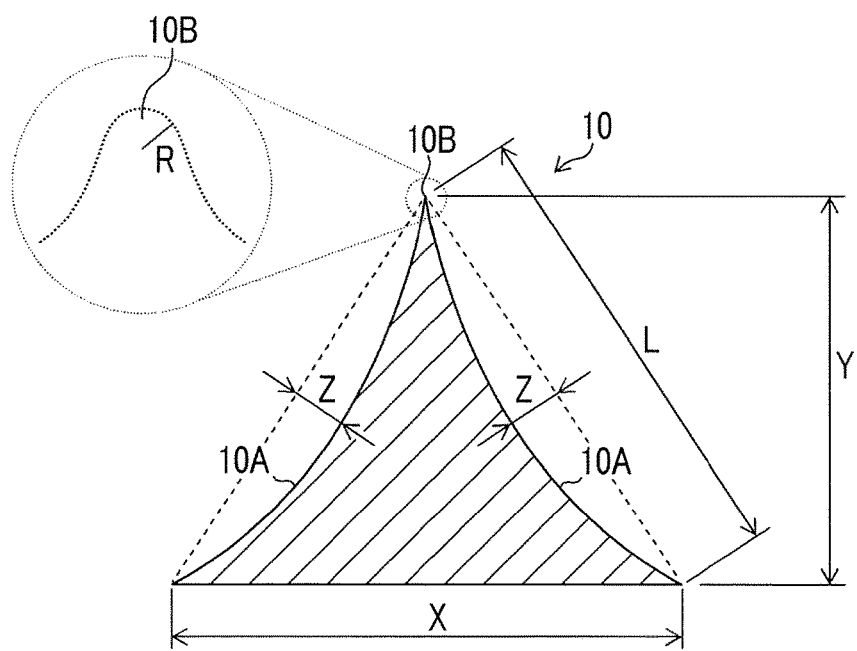
FIG. 2 is a cross-sectional view showing the pyramidal microneedle (needle-like protruding portion) of the transdermal absorption sheet.

The needle-like protruding portions (also referred to as microneedles) on a transdermal absorption sheet produced according to the embodiment will be described. FIG. 1 is a perspective view showing a pyramidal microneedle (needle-like protruding portion) on a transdermal absorption sheet, and FIG. 2 is a cross-sectional view. In the embodiment, example of a quadrangular pyramidal needle-like protruding portion is described, but the present invention is not limited to this shape.

As shown in FIGS. 1 and 2, it is preferable that the microneedle (needle-like protruding portion) 10 formed on the transdermal absorption sheet needs to be shaped as follows so as to be stuck several hundred μm deep into the surface of the skin: (1) the tip end is sufficiently pointed, and the diameter of the needle penetrating the skin is sufficiently small (the aspect ratio of length/diameter is high), and (2) the microneedle has a sufficient strength (the needle does not bend).

Thus, to meet the requirement in (1), a thin and pointed shape is needed. However, this is opposed to (2), and an excessively thin needle is bent at the tip end or root thereof, whereas an excessively thick needle fails to be stuck into the skin. Thus, as depicted in FIG. 1, a ridge line 10A of the microneedle 10 is preferably shaped to be curved toward the inside of the microneedle. The microneedle having such a shape can be made difficult to bend by sufficiently sharpening the tip end and widening the root. Further, the ridge lines 10A, 10A of a quadrangular pyramidal microneedle preferably extend from a quadrangular pyramidal surface 10C between the ridge lines.

The shape of the microneedle 10 is preferably formed such that a side X of a bottom surface is in a range of 0.1 μm or more and 1,000 μm or less, and the height is 0.3 μm or more and 3,000 μm or less. More preferably, the side X of the bottom surface is in a range of 10 μm or more and 400 μm or less and the height is 30 μm or more and 1,200 m or less.

When the length of a segment connecting a start point and an end point of the ridge line is represented as L, the maximum depth Z of curve of the ridge line 10A is preferably 0.04×L or more and 0.2×L or less. In addition, the radius of the curvature R of a microneedle tip end 10B, which indicates sharpness of the microneedle 10, is preferably 20 μm or less, and more preferably 15 μm or less.

Figure 3:
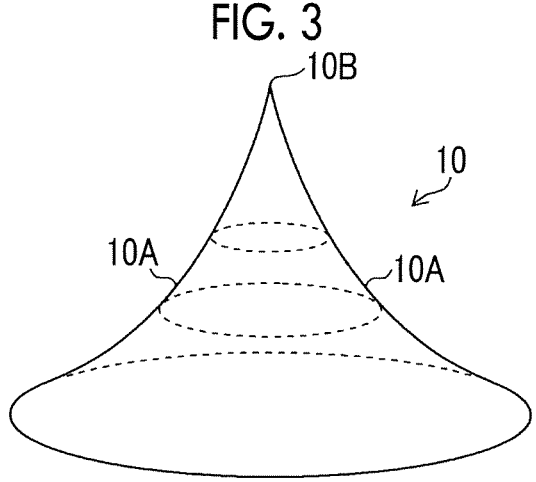
FIG. 3 is a perspective view showing a conical microneedle (needle-like protruding portion) of a transdermal absorption sheet.
Figure 4:
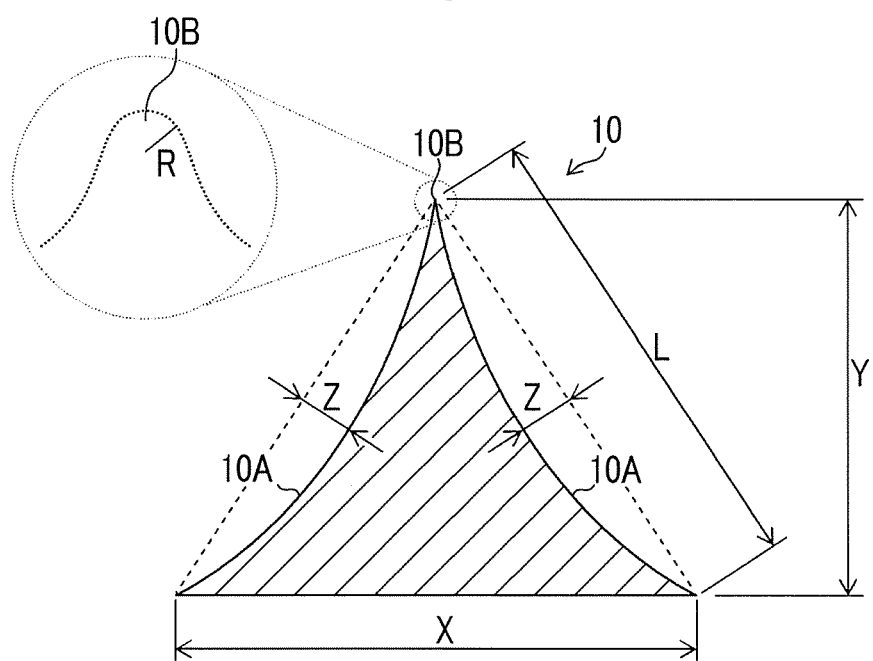
FIG. 4 is a cross-sectional view showing the conical microneedle (needle-like protruding portion) of the transdermal absorption sheet.

FIGS. 1 and 2 show the quadrangular pyramidal microneedle 10. However, a conical microneedle shown in FIGS. 3 and 4 and microneedles having other pyramids such as a triangular pyramid preferably have similar sizes. In the case of the conical shape, the diameter X of the bottom surface is preferably in a range of 0.1 μm or more and 1,000 μm or less, and more preferably in a range of 50 μm or more and 500 μm or less. In addition, when length of a segment connecting a start point and an end point of the generatrix of the conical surface is represented as L, the maximum depth Z of the curve of the conical surface is preferably 0.04×L or more and 0.2×L or less.

As described above, the transdermal absorption sheet forms a protruding portion array in which the microneedles are arranged in a two-dimensional array. In order to allow the microneedle to be easily stuck into the skin, it is important to sufficiently sharpen the microneedle tip end 10B. The radius of the curvature R of the microneedle tip end 10B is preferably 20 μm or less. In order to form a microneedle 10 having a tip end with a radius of curvature R of 20 μm or less, an important point is whether a solution of a polymer resin can be injected down to the tip end (bottom) of a needle-like recessed portion corresponding to an inverted shape of the protrusion array formed in the mold (die) to allow accurate transfer.

In addition, the transdermal absorption sheet needs to contain a drug, but many drugs are expensive. Thus, it is important to contain a drug in the transdermal absorption sheet such that the drug is concentrated at the portion of each microneedle and to fill the transdermal absorption sheet with the drug with high accuracy in terms of costs.

[Method of Producing Transdermal Absorption Sheet]

Next, a method of producing the sheet having a needle-like protruding portion according to the embodiment of the present invention will be described using a transdermal absorption sheet having a microneedle as an example.

(Preparation of Mold)

Figure 5:
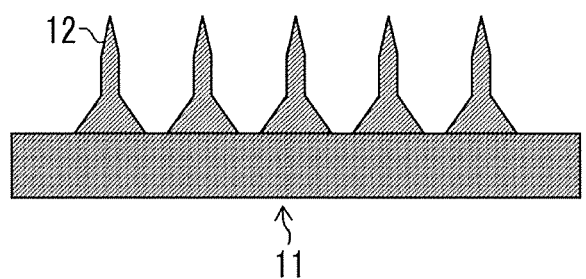
FIG. 5 is a step diagram of a method of producing a mold.
Figure 6:
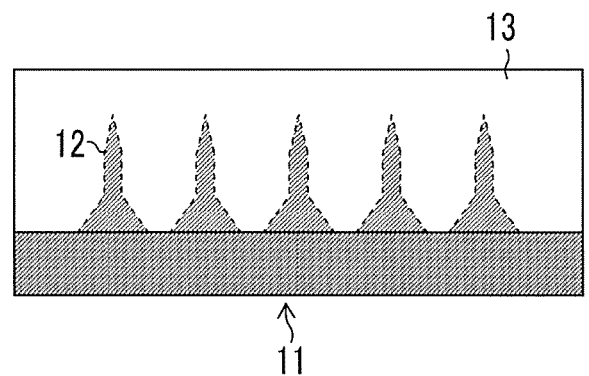
FIG. 6 is a step diagram of the method of producing the mold.
Figure 7:
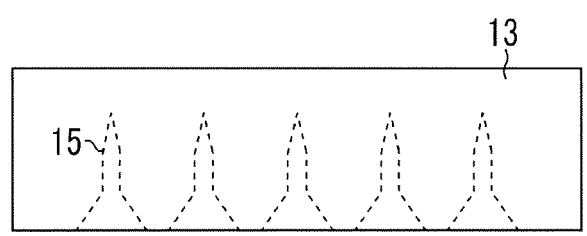
FIG. 7 is a step diagram of the method of producing the mold.

FIGS. 5 to 7 are step diagrams illustrating production of a mold (die).

As shown in FIG. 5, an original plate which is used to prepare a mold for producing the transdermal absorption sheet is first prepared.

Two types of methods for preparing an original plate 11 are available. A first method is a method of applying a photo resist to a Si substrate and then exposing and developing the photo resist. Then, etching such as reactive ion etching (RIE) is performed on the photo resist to prepare an array of conical shape portions (needle-like protruding portions) 12 on a surface of the original plate 11. When etching such as RIE is performed so as to form the conical shape portions on the surface of the original plate 11, the conical shapes can be formed by carrying out etching in an oblique direction while the Si substrate is being rotated.

A second method is a method of machining a metal substrate such as Ni using a cutting tool such as a diamond bit to form an array of the shape portions 12 shaped like quadrangular pyramids or the like on the surface of the original plate 11.

Next, the mold is prepared. Specifically, as shown in FIG. 6, the mold 13 is prepared from the original plate 11. Since the original plate 11 has the shape of cones or pyramids (such as quadrangular pyramids) with pointed tip ends, the following methods are conceived which enables to precisely transfer the shape of the original plate 11 to the mold 13 and then to peel off the mold 13 from the original plate 11, while producing the mold 13 at low cost.

A first method is a method of pouring, into the original plate 11, a silicone resin containing PDMS (polydimethylsiloxane, for example, SYLGARD 184, manufactured by Dow Corning Toray Co., Ltd.) with a curing agent added thereto, heating and curing the silicone resin at 100° C., and then peeling off the silicone resin from the original plate 11. A second method is a method of pouring, into the original plate 11, a UV (ultraviolet) curable resin that is curable by irradiation with ultraviolet light, irradiating the UV curable resin with ultraviolet light in a nitrogen atmosphere, and then peeling off the UV curable resin from the original plate 11. A third method is a method of pouring a solution of a plastic resin such as polystyrene or polymethylmethacrylate (PMMA) dissolved into an organic solvent, into the original plate 11 coated with a release agent, volatilizing the organic solvent by drying to cure the plastic resin, and then peeling off the plastic resin from the original plate 11.

Accordingly, the mold 13 in which needle-like recessed portions 15 that are inverted shapes of cones or pyramids on the original plate 11 are arranged in a two-dimensional array is prepared. The mold 13 prepared as described above is shown in FIG. 7. In addition, the mold 13 can be easily prepared any number of times using any of the above-described methods.

Figure 8:
FIG. 8 is a cross-sectional view showing a mold provided with a frame.
Figure 9:
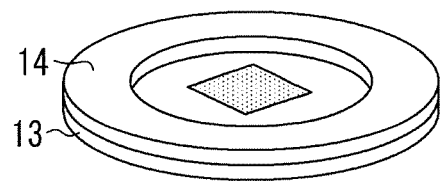
FIG. 9 is a perspective view showing the mold provided with the frame.

FIGS. 8 and 9 are diagrams shown that a frame 14 is placed on the mold. FIG. 8 is a cross-sectional view in a case in which the frame is provided at the periphery of the mold and FIG. 9 is a perspective view of the mold shown in FIG. 8. Provision of the frame 14 allows a solution of a polymer resin (hereinafter, also referred to as a "polymer solution") to be prevented from flowing out from the mold 13 when the transdermal absorption sheet is formed to have a desired film thickness.

At this time, a step between the mold 13 and the frame 14 is preferably 50 μm or more and 10 mm or less. In addition, the dies in FIGS. 8 and 9 are configured to enable the mold 13 and the frame 14 to be separated from each other, but the mold 13 and the frame 14 may be integrated together. In the case in which the mold and the frame are configured to be separable, the frame 14 can be removed in a drying step and a peeling-off step after a polymer solution filling step.

Figure 10:
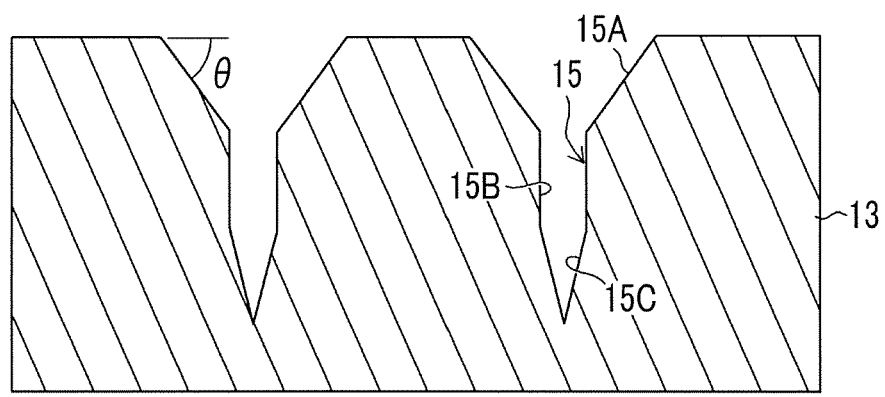
FIG. 10 is a cross-sectional view showing an embodiment of another mold.

FIG. 10 shows an embodiment of another preferable mold 13. The needle-like recessed portion 15 includes a tapered inlet portion 15A that becomes narrower in a depth direction from the surface of the mold 13, an intermediate recessed portion 15B with a constant width in the depth direction, and a tip end recessed portion 15C that is tapered in the depth direction. The angle θ of the taper is preferably in the range of 10° to 20°. The tapered inlet portion 15A allows the needle-like recessed portion 15 to be easily filled with the polymer solution.

Figure 11:
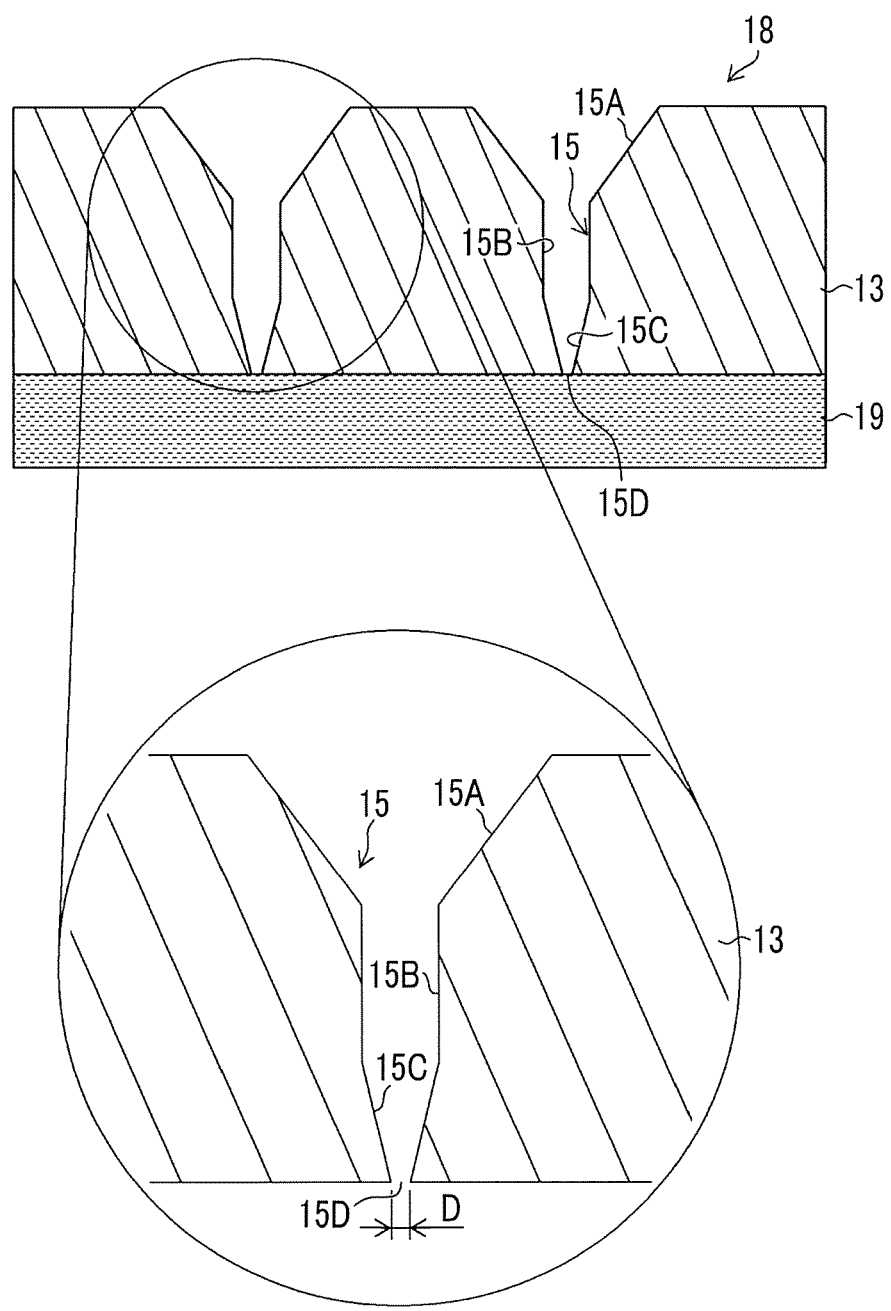
FIG. 11 is a cross-sectional view showing an embodiment of a mold complex.

FIG. 11 shows an embodiment of a mold complex 18 that is more preferable in executing the method of producing the transdermal absorption sheet.

As shown in FIG. 11, the mold complex 18 includes the mold 13 in which an air vent hole 15D is formed at the tip end (bottom) of each needle-like recessed portion 15 and a gas permeable sheet 19 laminated to a back surface of the mold 13 and formed of a material that allows gas to permeate, while preventing liquid from permeating. The air vent hole 15D is formed as a through-hole that penetrates the back surface of the mold 13. Here, the back surface of the mold 13 refers to a surface on the side of the mold 13 on which the air vent hole 15D is formed. Thus, a tip end of the needle-like recessed portion 15 communicates with the atmosphere via the air vent hole 15D and the gas permeable sheet 19.

The use of the mold complex 18 as described above allows only the air present in the needle-like recessed portions 15 to be driven out from the needle-like recessed portions 15 while preventing permeation of the transdermal absorption material solution filling the needle-like recessed portions 15. This improves transferability with which the shape of the needle-like recessed portion 15 is transferred to the transdermal absorption material and allows formation of sharper microneedles 10.

The diameter D (diameter) of the air vent hole 15D is preferably in the range of 1 to 50 μm. A diameter D of the air vent hole 15D of less than 1 μm fails to allow the air vent hole to sufficiently accomplish the functions thereof. A diameter D of the air vent hole 15D of more than 50 μm is likely to cause the sharpness of the tip end portion of the molded microneedle 10 to be degraded.

As a gas permeable sheet 19 formed of a material that allows gas to permeate while preventing liquid from permeating, for example, LATEX (Asahi-Kasei Chemicals Corporation) may be suitably used.

As the material used for the mold 13, an elastic raw material and a metallic raw material may be used. Among these, an elastic raw material is preferable and a raw material with high gas permeability is more preferable. The oxygen permeability, which is representative of the gas permeability, is preferably more than $1 \times 10^{-12}$ (mL/s·m·Pa) and more preferably more than $1 \times 10^{-10}$ (mL/s·m·Pa). Setting the gas permeability to be in the above range allows the air present in the needle-like recessed portions 15 in the mold 13 to be driven out from the mold 13 side, allowing production of a transdermal absorption sheet with few defects. Specifically, examples of such raw material include materials obtained by melting a silicone resin (for example, SYLGARD 184 or 1310ST), a UV curable resin, or a plastic resin (for example, polystyrene or polymethylmethacrylate (PMMA)), and materials obtained by dissolving any of above resins into a solvent. Among these, a silicone rubber-based raw material can be suitably used because of the durability thereof against transfers by repeated pressurization and the good peelability thereof from the raw material. In addition, examples of the metallic raw material include Ni, Cu, Cr, Mo, W, Ir, Tr, Fe, Co, MgO, Ti, Zr, Hf, V, Nb, Ta, α-aluminum oxide, zirconium oxide, stainless steel (STAVAX material), and alloys thereof. For the material of the frame 14, a material similar to the material of the mold 13 may be used.

(Polymer Solution)

The polymer solution that is a solution of the polymer resin used for the material of the transdermal absorption sheet in the embodiment is described.

As the raw material for the resin polymer used for the polymer solution, a biocompatible resin is preferably used. It is preferable to use, as such a resin, sugar such as glucose, maltose, pullulan, dextran, sodium chondroitin sulfate, sodium hyaluronate, hydroxypropyl cellulose, or hydroxyethyl starch, protein such as gelatin, or a biodegradable polymer such as polylactic acid and a lactic acid-glycolic acid copolymer. Among these, sodium chondroitin sulfate, hydroxypropyl cellulose, or dextran can be suitably used. In addition, gelatin-based raw materials have an adhesion with many base materials and have a high gel strength as materials to be gelated. Thus, in a peeling-off step to be described below, the materials can be brought into tight contact with the base material to allow the polymer sheet to be peeled off from the mold using the base material. Although the concentration varies depending on the material, it is preferable to be such a concentration that 10% to 50% of the resin polymer is contained in the solution. In addition, a solvent to be used for the dissolution may be other than warm water if it has volatility, and methyl ethyl ketone (MEK), alcohol, or the like can be used. A drug to be supplied to the inside of the human body may concurrently be dissolved into a solution of the polymer resin in accordance with the application.

For a method of preparing the polymer solution, in the case of using a water-soluble polymer (gelatin or the like), the solution can be prepared by dissolving a water-soluble powder into water, and after the dissolution, adding a drug to the solution. In the case in which the material is difficult to dissolve into water, the material may be dissolved by heating. The temperature may be selected appropriately depending on the type of the polymer material, but the material is preferably heated at a temperature of about 60° C. or lower. Further, in the case in which a thermally melted polymer (maltose or the like) is used, the solution can be prepared by melting the raw material and the drug on heating. The heating temperature is preferably a temperature at which the raw material is melted, and is specifically about 150° C.

The viscosity of the solution of the polymer resin is preferably 2,000 Pa·s or less and more preferably 1,000 Pa·s or less. Appropriate adjustment of the viscosity of the solution of the polymer resin facilitates injection of the solution into the recessed portions of the mold. In addition, the viscosity of the drug-containing solution is preferably 100 Pa·s or less and more preferably 10 Pa·s or less.

(Drug)

The drug is not limited as long as the drug has the functions as a drug. Particularly, the drug is preferably selected from the group consisting of peptide, protein, nucleic acid, polysaccharide, a vaccine, a medical compound belonging to a water-soluble low-molecular-weight compound, and a cosmetic component. As the water-soluble polymer substance contained in the drug-containing layer, one that does not interact with the drug contained in the layer is preferably used. For example, in the case of using protein as the drug, when a chargeable polymer substance is mixed with the protein, the protein and the polymer substance electrostatically interact with each other to form an aggregate, which is cohered and precipitated. Therefore, in the case in which a chargeable substance is used in the drug, a water-soluble polymer substance with no charge such as hydroxyethyl starch or dextran is preferably used.

<Production of Transdermal Absorption Sheet>

A method of producing the transdermal absorption sheet using the mold 13 produced as described above will be described. In the following description, a method of separately feeding the drug-containing solution and the polymer solution to the mold will be described.

Figure 12:
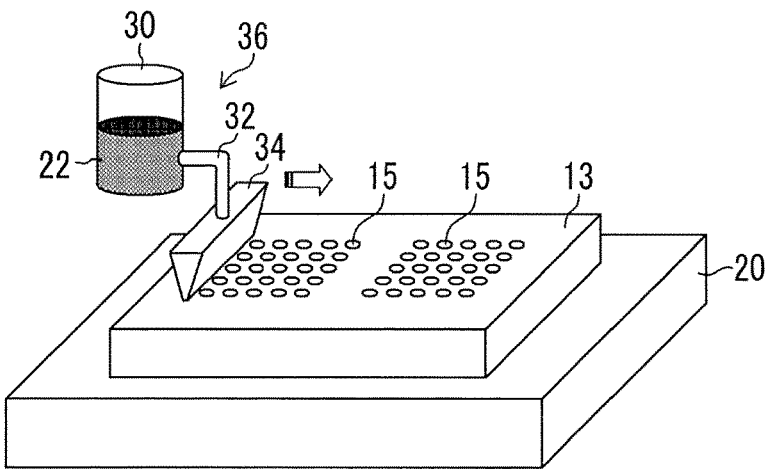
FIG. 12 is a schematic view showing a drug solution filling step.
Figure 13:
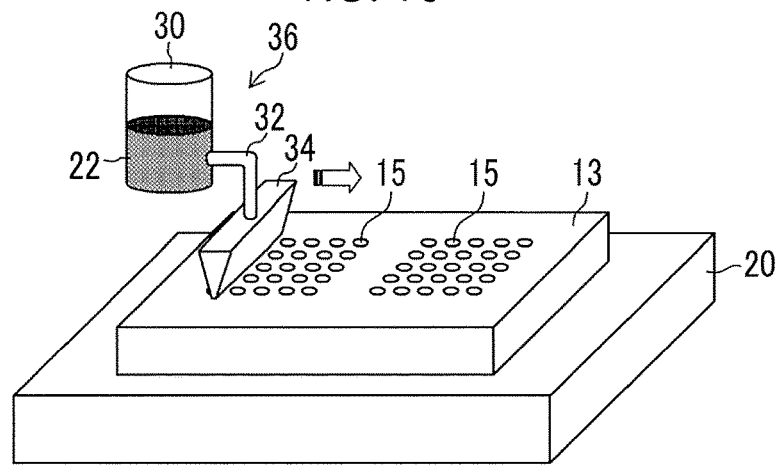
FIG. 13 is a schematic view showing the drug solution filling step.
Figure 14:
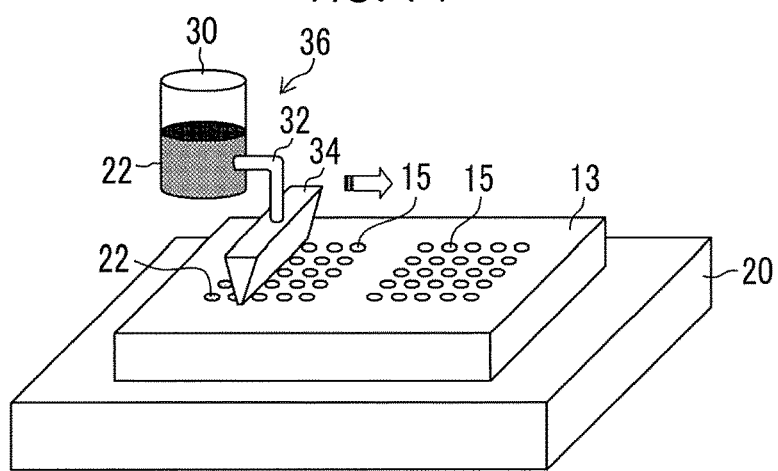
FIG. 14 is a schematic view showing the drug solution filling step.

FIGS. 12 to 14 are views showing a drug solution filling step. As shown in FIG. 12, first, the mold 13 with the two-dimensionally arranged needle-like recessed portions 15 is placed on a base 20. Two sets of a plurality of needle-like recessed portions 15, each set including 5×5 two-dimensionally arranged needle-like recessed portions 15, are formed in the mold 13. A liquid feeding apparatus 36 which has a tank 30 housing a drug-containing solution 22, a pipe 32 connected to the tank, and a nozzle 34 connected to a tip end of the pipe 32 is prepared.

Figure 15:
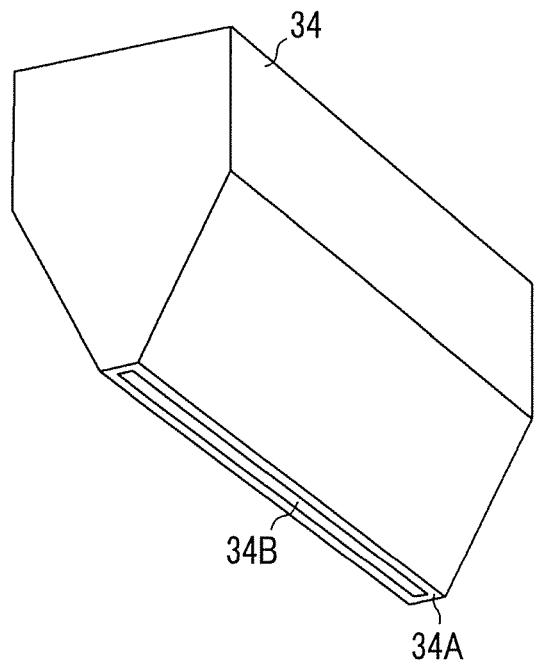
FIG. 15 is a perspective view showing a tip end portion of a nozzle.

FIG. 15 shows a schematic perspective view of the tip end portion of the nozzle. As shown in FIG. 15, the tip end of the nozzle 34 includes a lip portion 34A that is a flat surface and a slit-shaped opening portion 34B. The slit-shaped opening portion 34B, for example, allows a plurality of needle-like recessed portions 15 constituting one column to be simultaneously filled with the drug-containing solution 22. The size (length and width) of the opening portion 34B is appropriately selected in accordance with the number of needle-like recessed portions 15 to be filled at a time.

An increased length of the opening portion 34B makes it possible to fill an increased number of needle-like recessed portions 15 with the drug-containing solution 22 at a time. Thus, productivity can be improved.

Figure 16:
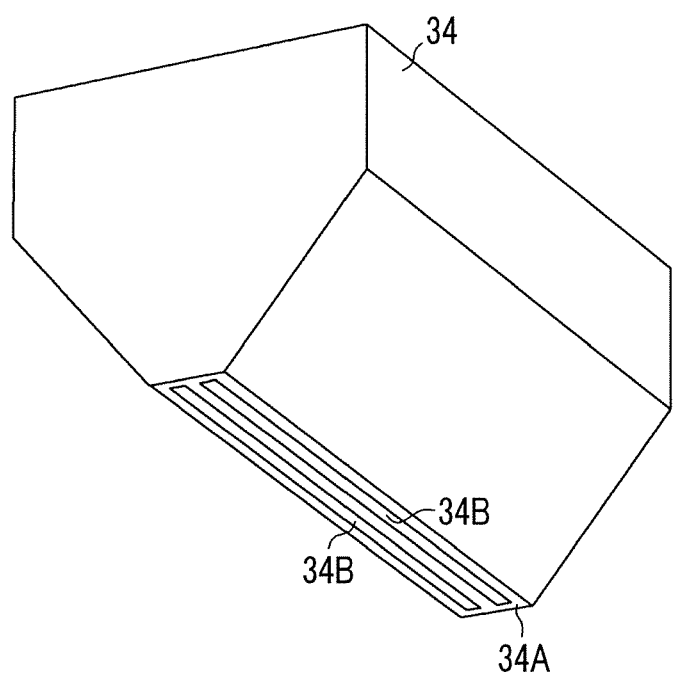
FIG. 16 is a perspective view showing a tip end portion of another nozzle.

FIG. 16 shows a schematic perspective view of a tip end portion of another nozzle. As shown in FIG. 16, the lip portion 34A at the tip end of the nozzle 34 has two slit-shaped opening portions 34B. The two opening portions 34B, for example, allow a plurality of needle-like recessed portions 15 constituting two columns to be simultaneously filled with the drug-containing solution 22.

As the material used for the nozzle 34, an elastic raw material and a metallic raw material may be used. For example, TEFLON (registered trademark), stainless steel, or titanium may be used.

A drug solution filling step will be described with reference to FIG. 13. As shown in FIG. 13, the position of the opening portion 34B in the nozzle 34 is adjusted over the needle-like recessed portions 15. The lip portion 34A of the nozzle 34 is in contact with the surface of the mold 13. The drug-containing solution 22 is fed from the liquid feeding apparatus 36 to the mold 13, and the needle-like recessed portions 15 are filled with the drug-containing solution 22 through the opening portion 34B in the nozzle 34. In the embodiment, a plurality of needle-like recessed portions 15 constituting one column are simultaneously filled with the drug-containing solution 22. However, the present invention is not limited to this configuration. The needle-like recessed portions 15 may be filled with the drug-containing solution 22 one by one. In addition, by using the nozzle 34 shown in FIG. 16, a plurality of needle-like recessed portions 15 constituting a plurality of columns can be simultaneously filled with the drug-containing solution 22 so that filling is performed on a plurality of columns at a time.

In the case in which the mold 13 is constituted of a raw material having gas permeability, the drug-containing solution 22 can be sucked by sucking from the back surface of the mold 13, thereby promoting filling of the inside of the needle-like recessed portions 15 with the drug-containing solution 22.

Next, as shown in FIG. 14, while brining the lip portion 34A of the nozzle 34 into contact with the surface of the mold 13, the liquid feeding apparatus 36 is relatively moved in a direction perpendicular to a length direction of the opening portion 34B, to move the nozzle 34 to the needle-like recessed portions 15 not filled with the drug-containing solution 22. The position of the opening portion 34B in the nozzle 34 is adjusted over the needle-like recessed portions 15. The embodiment has been described with reference to the example in which the nozzle 34 is moved. However, the mold 13 may be moved.

Since the nozzle 34 is moved with the lip portion 34A of the nozzle 34 and the surface of the mold 13 in contact with each other, the nozzle 34 can scrape off the drug-containing solution 22 remaining on the surface of the mold 13 except on the needle-like recessed portions 15. This enables the drug-containing solution 22 to be prevented from remaining on the mold 13 except on the needle-like recessed portions 15.

The filling of the drug-containing solution 22 in FIG. 11 and the moving of the nozzle 34 in FIG. 12 are repeated to fill the 5×5 two-dimensionally arranged needle-like recessed portions 15 with the drug-containing solution 22. When the 5×5 two-dimensionally arranged needle-like recessed portions 15 are filled with the drug-containing solution 22, the liquid feeding apparatus 36 is moved to the adjacent 5×5 two-dimensionally arranged needle-like recessed portions 15, and the filling of the drug-containing solution 22 in FIG. 11 and the moving of the nozzle 34 in FIG. 12 are repeated. The adjacent 5×5 two-dimensionally arranged needle-like recessed portions 15 are also filled with the drug-containing solution 22.

The above-described filling of the drug-containing solution 22 and the moving of the nozzle 34 may be in (1) a form in which the needle-like recessed portions 15 are filled with the drug-containing solution 22 while the nozzle 34 is being moved or (2) a form in which, while the nozzle 34 is in motion, the nozzle 34 is temporarily stopped over the needle-like recessed portions 15 to fill the needle-like recessed portions 15 with the drug-containing solution 22, and the nozzle 34 is moved again after the filling. Between the filling of the drug-containing solution 22 and the moving of the nozzle 34, the lip portion 34A of the nozzle 34 is in contact with the surface of the mold 13.

Figure 17:
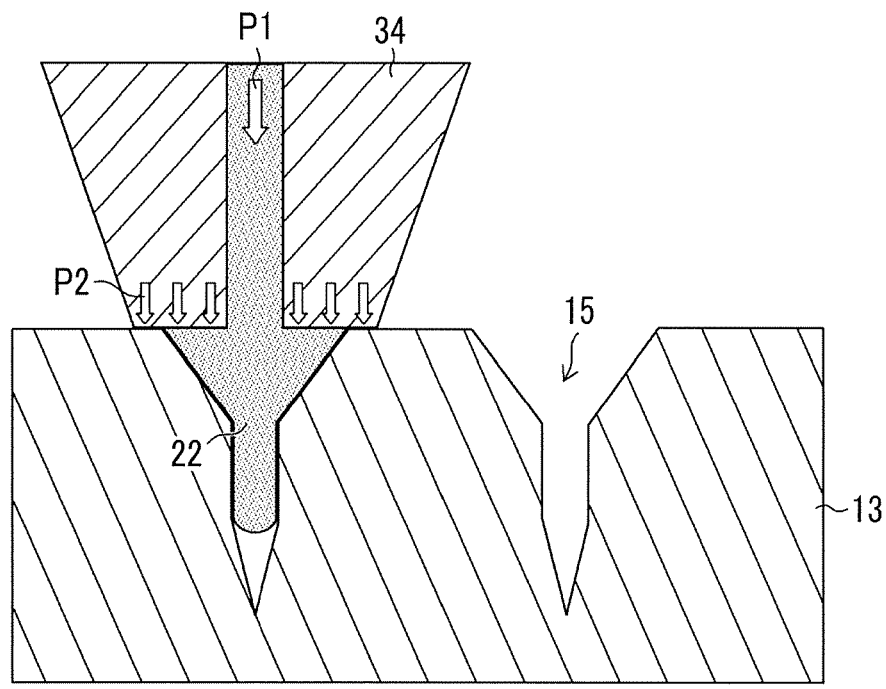
FIG. 17 is a partially enlarged view showing the tip end of the nozzle and the mold while filling.

FIG. 17 is a partially enlarged view of the tip end of the nozzle 34 and the mold 13 during filling of the needle-like recessed portions 15 with the drug-containing solution 22. As shown in FIG. 17, filling of the inside of the needle-like recessed portions 15 with the drug-containing solution 22 can be promoted by applying a pressuring force P1 into the nozzle 34. Further, when the inside of the needle-like recessed portions 15 is filled with the drug-containing solution 22, a pressing force P2 with which the nozzle 34 is brought into contact with the surface of the mold 13 is preferably set to be equal to or stronger than the pressuring force P1 in the nozzle 34. Setting the pressing force P2≥the pressuring force P1 enables the drug-containing solution 22 to be restrained from leaking from the needle-like recessed portions 15 to the surface of the mold 13.

Figure 18:
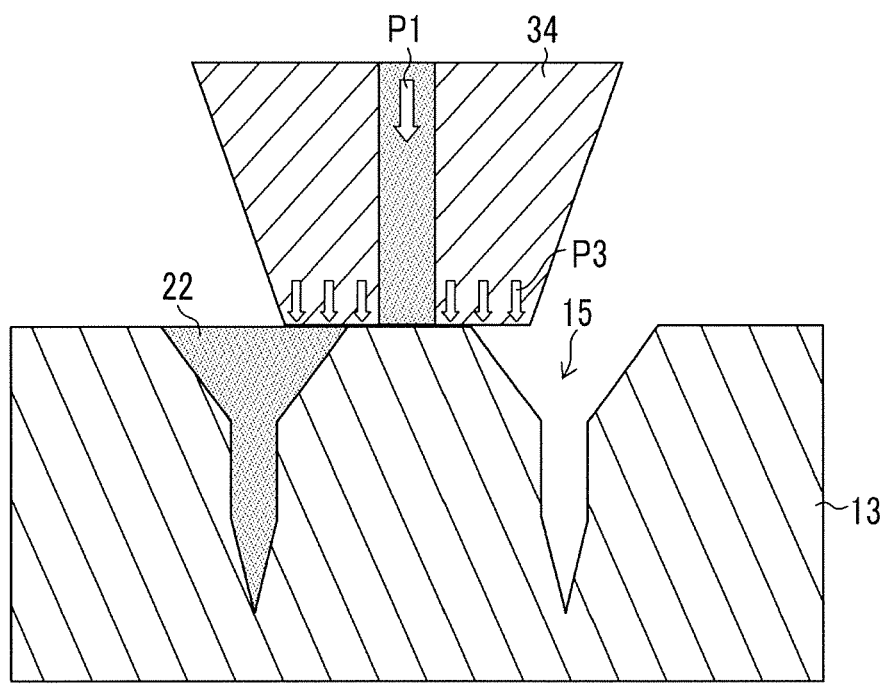
FIG. 18 is a partially enlarged view showing the tip end of the nozzle and the mold while moving.

FIG. 18 is a partially enlarged view of the tip end of the nozzle 34 and the mold 13 during movement of the nozzle 34. When the nozzle 34 is moved relative to the mold 13, a pressing force P3 with which the nozzle 34 is brought into contact with the surface of the mold 13 is preferably set to be weaker than the pressing force P2 with which the nozzle 34 is brought into contact with the surface of the mold 13 while filling is performed. This is intended to reduce damage to the mold 13 and to suppress deformation of the mold 13 associated with compression.

Figure 19:
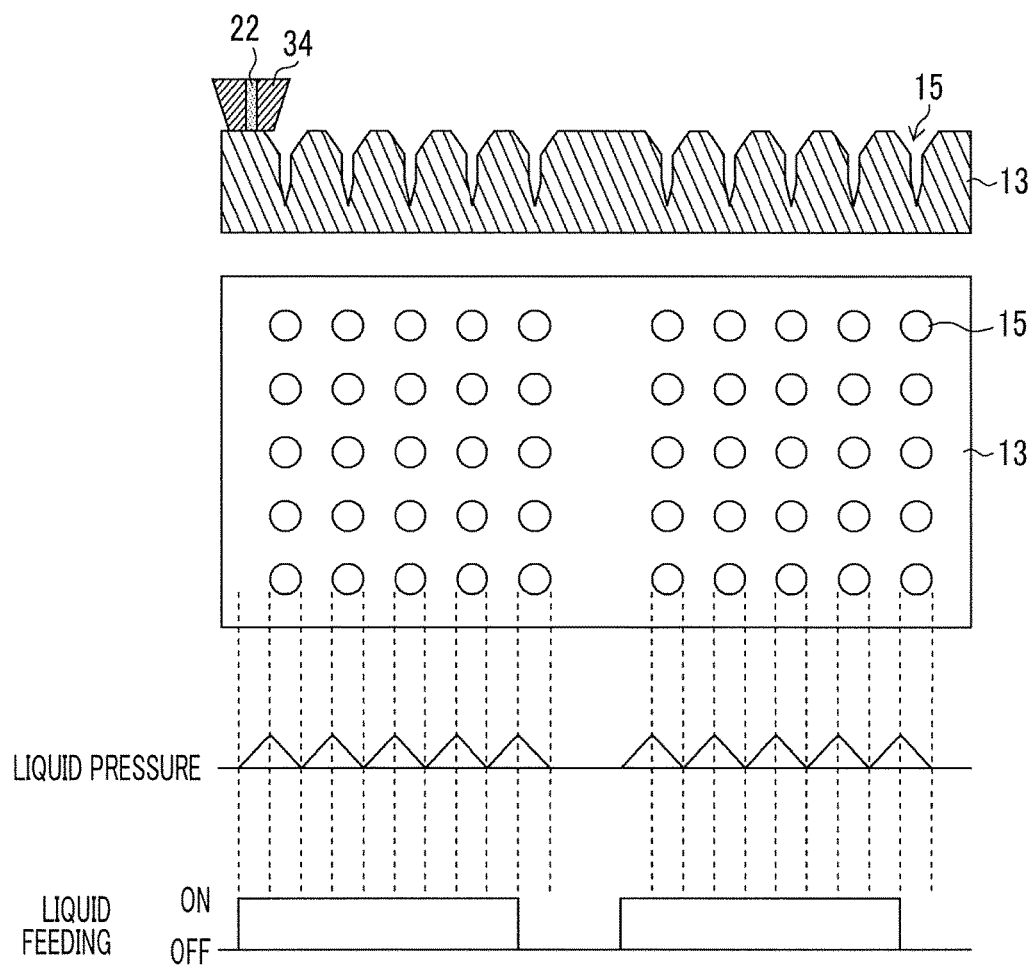
FIG. 19 is a diagram illustrating the relation between the liquid pressure in the nozzle and feeding of the drug-containing solution.

FIG. 19 is a diagram illustrating the relation between the liquid pressure in the nozzle and feeding of the drug-containing solution. As shown in FIG. 19, feeding of the drug-containing solution 22 is started before the nozzle 34 is positioned over the needle-like recessed portions 15. This is intended to reliably fill the needle-like recessed portions 15 with the drug-containing solution 22. The drug-containing solution 22 is continuously fed to the mold 13 until the filling of the plurality of needle-like recessed portions 15 constituted of the 5×5 needle-like recessed portions 15 is completed. The feeding of the drug-containing solution 22 to the mold 13 is stopped before the nozzle 34 is positioned over the fifth column of the needle-like recessed portions 15. Then, the drug-containing solution 22 can be prevented from overflowing the needle-like recessed portions 15. When the feeding of the drug-containing solution 22 is started, the liquid pressure in the nozzle 34 is elevated in areas where the nozzle 34 is not positioned over the needle-like recessed portions 15. On the other hand, when the nozzle 34 is positioned over the needle-like recessed portions 15, the needle-like recessed portions 15 are filled with the drug-containing solution 22 to lower the liquid pressure in the nozzle 34. The variation in liquid pressure is repeated.

When the filling of the plurality of needle-like recessed portions 15 constituted of the 5×5 needle-like recessed portions 15 is completed, the nozzle 34 is moved to the adjacent plurality of needle-like recessed portions 15 constituted of the 5×5 needle-like recessed portions 15. For the liquid feeding, the feeding of the drug-containing solution 22 is preferably stopped at the time of movement to the adjacent plurality of needle-like recessed portions 15 constituted of the 5×5 needle-like recessed portions 15. A distance between the fifth column of needle-like recessed portions 15 and the next first column of needle-like recessed portions 15 is long. When the drug-containing solution 22 is continuously fed while the nozzle 34 is moving between the fifth column of needle-like recessed portions and the next first column of needle-like recessed portions, there is a case in which the liquid pressure in the nozzle 34 may be excessively high. As a result, a case in which the drug-containing solution 22 flows out from the nozzle 34 onto an area other than the needle-like recessed portions 15 in the mold 13 may occur. In order to prevent this case, it is preferable that the feeding of the drug-containing solution 22 is stopped.

When the filling of the needle-like recessed portions 15 with the drug-containing solution 22 is completed, the process proceeds to a step of forming a polymer sheet with needle-like protruding portions each formed on a surface of the sheet, the polymer sheet including a drug-containing layer constituted of the drug-containing solution 22 and a non-drug-containing layer constituted of a non-drug-containing solution. The needle-like protruding portions have inverted shapes of the needle-like recessed portions.

The above-described drug solution filling step is performed by pressing the tip end of the nozzle 34 against the mold to pressurize the inside of the nozzle 34 but is not limited to this method. For example, when the drug-containing solution is fed over the mold using a nozzle, a dispenser, or the like, and a blade is moved while being brought into contact with the surface of the mold, the needle-like recessed portions can be filled with the drug-containing solution.

Figure 20:
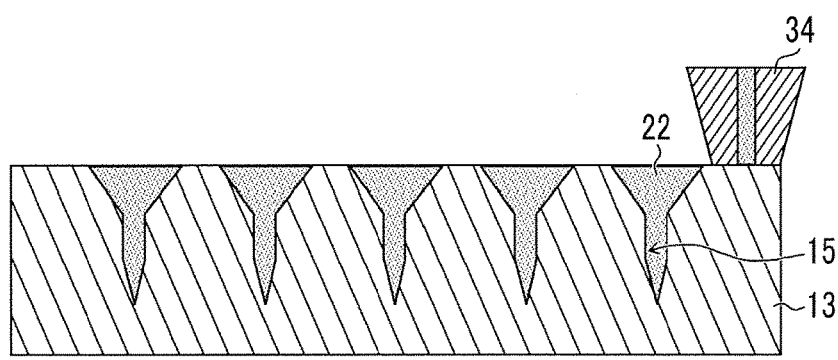
FIG. 20 is a diagram illustrating a step of forming a polymer sheet.

Several embodiments of the polymer solution filling step and the polymer solution drying step will be described. A first embodiment is described with reference to FIGS. 20 to 22. As shown in FIG. 20, the needle-like recessed portions 15 of the mold 13 are filled with the drug-containing solution 22. For the filling method, as shown in FIGS. 12 to 14, filling can be performed with contact of the tip end portion of the nozzle with the mold. Next, as shown in FIG. 21, a polymer solution 24 is applied onto the drug-containing solution 22 using a dispenser. In addition to the application using the dispenser, for example, a bar coating method, a spin coating method, and an application using a spray or the like can be applied.

Next, as shown in FIG. 22, the drug-containing solution 22 and the polymer solution 24 are dried and solidified to form a polymer sheet 1 including a drug-containing layer 26 and a non-drug-containing layer (polymer layer) 28.

In the embodiment, in the step of drying and solidifying the drug-containing solution 22 and the polymer solution 24, the drying conditions are controlled. The control of the drying conditions is performed by controlling an average solid content concentration in the polymer solution. The variation in average solid content concentration can be calculated by measuring a variation in weight in the drying step. The drying conditions in a concentration range in which the average solid content concentration in the polymer solution is 70 wt % or more and 80 wt % or less in terms of weight percent are set as low rate drying conditions. The concentration range in which the average solid content concentration in the polymer solution is 70 wt % or more and 80 wt % or less is a range in which the polymer solution gradually loses its fluidity, and in the embodiment, when the drying conditions in the concentration range in which the average solid content concentration is 70 wt % or more and 80 wt % or less is set as low rate drying conditions, the shape of the needle-like protruding portion can be prevented from being deformed by rapid drying.

In addition, when a constant drying rate of water is obtained based on Tables 1 and 2 below and the constant drying rate of water is used as an index, in a concentration range in which the average solid content concentration in the polymer solution is 70 wt % or more and 80 wt % or less in terms of weight percent, the constant drying rate is set to be lower than the maximum value of the constant drying rate in the concentration range in which the average solid content concentration is less than 70 wt % and more than 80 wt %. The range in which the drying conditions are low rate drying conditions and the range in which the constant drying rate is low are more preferably a concentration range in which the solid content concentration is 60 wt % or more and 85 wt % or less.

For the constant drying rate, wet bulb humidity is obtained from dry bulb humidity and relative humidity of the drying conditions. The constant drying rate can be obtained from the dry bulb humidity and the wet bulb humidity from Table 1. The values in Table 2 are values obtained when the wind speed is set to 0.4 m/s.

TABLE 1

| | | Dry bulb temperature ° C. | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| | | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 | 45 |
| Wet bulb temperature ° C. | 5 | 11% | 7% | 3% | | | | | | | | | | | | | | | | | | | | | | | | | | | | |
| | 6 | 19% | 14% | 10% | 6% | 3% | | | | | | | | | | | | | | | | | | | | | | | | | | |
| | 7 | 27% | 22% | 17% | 13% | 9% | 5% | 2% | | | | | | | | | | | | | | | | | | | | | | | | |
| | 8 | 35% | 29% | 24% | 19% | 15% | 11% | 8% | 5% | 2% | | | | | | | | | | | | | | | | | | | | | | |
| | 9 | 43% | 37% | 31% | 26% | 22% | 17% | 14% | 10% | 7% | 5% | 2% | 0% | | | | | | | | | | | | | | | | | | | |
| | 10 | 52% | 45% | 39% | 33% | 28% | 24% | 20% | 16% | 13% | 10% | 7% | 5% | 2% | 0% | | | | | | | | | | | | | | | | | |
| | 11 | 61% | 54% | 47% | 41% | 35% | 30% | 26% | 22% | 18% | 15% | 12% | 9% | 7% | 5% | 3% | 1% | | | | | | | | | | | | | | | |
| | 12 | 70% | 62% | 55% | 48% | 42% | 37% | 32% | 28% | 24% | 20% | 17% | 14% | 11% | 9% | 7% | 5% | 3% | 1% | | | | | | | | | | | | | |
| | 13 | 80% | 72% | 64% | 56% | 50% | 44% | 39% | 34% | 29% | 25% | 22% | 19% | 16% | 13% | 11% | 8% | 6% | 5% | 3% | 2% | 0% | | | | | | | | | | |
| | 14 | 90% | 81% | 72% | 64% | 57% | 51% | 46% | 40% | 35% | 31% | 27% | 24% | 20% | 18% | 15% | 12% | 10% | 8% | 6% | 5% | 3% | 2% | 1% | | | | | | | | |
| | 15 | 100% | 90% | 81% | 73% | 65% | 59% | 53% | 47% | 42% | 37% | 33% | 29% | 25% | 22% | 19% | 17% | 14% | 12% | 10% | 8% | 6% | 5% | 4% | 2% | 1% | 0% | | | | | |
| | 16 | | 100% | 91% | 82% | 74% | 67% | 60% | 54% | 48% | 43% | 38% | 34% | 30% | 27% | 24% | 21% | 18% | 16% | 14% | 12% | 10% | 8% | 7% | 5% | 4% | 3% | 2% | 1% | 0% | | |
| | 17 | | | 100% | 91% | 82% | 75% | 67% | 61% | 55% | 49% | 44% | 40% | 36% | 32% | 28% | 25% | 22% | 20% | 17% | 15% | 13% | 11% | 10% | 8% | 7% | 5% | 4% | 3% | 2% | 1% | 1% |
| | 18 | | | | 100% | 91% | 83% | 75% | 68% | 62% | 56% | 50% | 46% | 41% | 37% | 33% | 30% | 27% | 24% | 21% | 19% | 16% | 14% | 13% | 11% | 9% | 8% | 7% | 6% | 5% | 4% | 3% |
| | 19 | | | | | 100% | 91% | 83% | 76% | 69% | 62% | 57% | 52% | 47% | 42% | 38% | 35% | 31% | 28% | 25% | 22% | 20% | 18% | 16% | 14% | 12% | 11% | 9% | 8% | 7% | 6% | 5% |
| | 20 | | | | | | 100% | 92% | 84% | 76% | 69% | 63% | 58% | 53% | 48% | 43% | 39% | 36% | 32% | 29% | 26% | 24% | 21% | 19% | 17% | 15% | 14% | 12% | 11% | 9% | 8% | 7% |
| | 21 | | | | | | | 100% | 92% | 84% | 77% | 70% | 64% | 59% | 54% | 49% | 45% | 41% | 37% | 34% | 30% | 28% | 25% | 23% | 20% | 18% | 17% | 15% | 13% | 12% | 10% | 9% |
| | 22 | | | | | | | | 100% | 92% | 84% | 77% | 71% | 65% | 60% | 54% | 50% | 46% | 42% | 38% | 35% | 32% | 29% | 26% | 24% | 22% | 20% | 18% | 16% | 14% | 13% | 12% |
| | 23 | | | | | | | | | 100% | 92% | 84% | 78% | 72% | 66% | 60% | 55% | 51% | 46% | 43% | 39% | 36% | 33% | 30% | 27% | 25% | 23% | 21% | 19% | 17% | 15% | 14% |
| | 24 | | | | | | | | | | 100% | 92% | 85% | 78% | 72% | 66% | 61% | 56% | 52% | 47% | 44% | 40% | 37% | 34% | 31% | 28% | 26% | 24% | 22% | 20% | 18% | 16% |
| | 25 | | | | | | | | | | | 100% | 92% | 85% | 79% | 73% | 67% | 62% | 57% | 52% | 48% | 44% | 41% | 38% | 35% | 32% | 29% | 27% | 25% | 23% | 21% | 19% |
| | 26 | | | | | | | | | | | | 100% | 93% | 86% | 79% | 73% | 67% | 62% | 58% | 53% | 49% | 45% | 42% | 39% | 36% | 33% | 30% | 28% | 26% | 24% | 22% |
| | 27 | | | | | | | | | | | | | 100% | 93% | 86% | 79% | 73% | 68% | 63% | 58% | 54% | 50% | 46% | 43% | 40% | 37% | 34% | 31% | 29% | 27% | 25% |
| | 28 | | | | | | | | | | | | | | 100% | 93% | 86% | 80% | 74% | 69% | 64% | 59% | 55% | 51% | 47% | 44% | 40% | 37% | 35% | 32% | 30% | 28% |
| | 29 | | | | | | | | | | | | | | | 100% | 93% | 86% | 80% | 74% | 69% | 64% | 60% | 55% | 51% | 48% | 44% | 41% | 38% | 36% | 33% | 31% |
| | 30 | | | | | | | | | | | | | | | | 100% | 93% | 86% | 80% | 75% | 69% | 65% | 60% | 56% | 52% | 48% | 45% | 42% | 39% | 36% | 34% |
| | 31 | | | | | | | | | | | | | | | | | 100% | 93% | 87% | 81% | 75% | 70% | 65% | 61% | 57% | 53% | 49% | 46% | 43% | 40% | 37% |
| | 32 | | | | | | | | | | | | | | | | | | 100% | 93% | 87% | 81% | 75% | 70% | 66% | 61% | 57% | 53% | 50% | 47% | 43% | 41% |
| | 33 | | | | | | | | | | | | | | | | | | | 100% | 93% | 87% | 81% | 76% | 71% | 66% | 62% | 58% | 54% | 50% | 47% | 44% |
| | 34 | | | | | | | | | | | | | | | | | | | | 100% | 93% | 87% | 81% | 76% | 71% | 67% | 62% | 58% | 55% | 51% | 48% |
| | 35 | | | | | | | | | | | | | | | | | | | | | | | | | | | | | | | |
| | 36 | | | | | | | | | | | | | | | | | | | | | | | | | | | | | | | |
| | 37 | | | | | | | | | | | | | | | | | | | | | | | | | | | | | | | |
| | 38 | | | | | | | | | | | | | | | | | | | | | | | | | | | | | | | |
| | 39 | | | | | | | | | | | | | | | | | | | | | | | | | | | | | | | |
| | 40 | | | | | | | | | | | | | | | | | | | | | | | | | | | | | | | |
| | 41 | | | | | | | | | | | | | | | | | | | | | | | | | | | | | | | |
| | 42 | | | | | | | | | | | | | | | | | | | | | | | | | | | | | | | |
| | 43 | | | | | | | | | | | | | | | | | | | | | | | | | | | | | | | |
| | 44 | | | | | | | | | | | | | | | | | | | | | | | | | | | | | | | |
| | 45 | | | | | | | | | | | | | | | | | | | | | | | | | | | | | | | |

TABLE 1-continued

| | 35 | 36 | 37 | 38 | 39 | 40 | 41 | 42 | 43 | 44 | 45 |
|---|---|---|---|---|---|---|---|---|---|---|---|
| 35 | 100% | 93% | 87% | 82% | 77% | 72% | 67% | 63% | 59% | 55% | 52% |
| 36 | | 100% | 94% | 88% | 82% | 77% | 72% | 68% | 63% | 59% | 56% |
| 37 | | | 100% | 94% | 88% | 82% | 77% | 72% | 68% | 64% | 60% |
| 38 | | | | 100% | 94% | 88% | 83% | 77% | 73% | 68% | 64% |
| 39 | | | | | 100% | 94% | 88% | 83% | 78% | 73% | 69% |
| 40 | | | | | | 100% | 94% | 88% | 83% | 78% | 73% |
| 41 | | | | | | | 100% | 94% | 88% | 83% | 78% |
| 42 | | | | | | | | 100% | 94% | 89% | 83% |
| 43 | | | | | | | | | 100% | 94% | 89% |
| 44 | | | | | | | | | | 100% | 94% |
| 45 | | | | | | | | | | | 100% |

TABLE 2

| | | Dry bulb temperature ° C. | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| | | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 | 45 |
| Wet bulb temperature ° C. | 5 | 0.17 | 0.19 | 0.20 | 0.22 | 0.24 | 0.26 | 0.27 | 0.29 | 0.31 | 0.33 | 0.34 | 0.36 | 0.38 | 0.40 | 0.41 | 0.43 | 0.45 | 0.47 | 0.48 | 0.50 | 0.52 | 0.54 | 0.56 | 0.57 | 0.59 | 0.61 | 0.63 | 0.65 | 0.66 | 0.68 | 0.70 |
| | 6 | 0.15 | 0.17 | 0.19 | 0.20 | 0.22 | 0.24 | 0.26 | 0.27 | 0.29 | 0.31 | 0.33 | 0.34 | 0.36 | 0.38 | 0.40 | 0.41 | 0.43 | 0.45 | 0.47 | 0.48 | 0.50 | 0.52 | 0.54 | 0.56 | 0.57 | 0.59 | 0.61 | 0.63 | 0.65 | 0.66 | 0.68 |
| | 7 | 0.14 | 0.15 | 0.17 | 0.19 | 0.20 | 0.22 | 0.24 | 0.26 | 0.27 | 0.29 | 0.31 | 0.33 | 0.34 | 0.36 | 0.38 | 0.40 | 0.41 | 0.43 | 0.45 | 0.47 | 0.49 | 0.50 | 0.52 | 0.54 | 0.56 | 0.57 | 0.59 | 0.61 | 0.63 | 0.65 | 0.67 |
| | 8 | 0.12 | 0.14 | 0.15 | 0.17 | 0.19 | 0.20 | 0.22 | 0.24 | 0.26 | 0.27 | 0.29 | 0.31 | 0.33 | 0.34 | 0.36 | 0.38 | 0.40 | 0.41 | 0.43 | 0.45 | 0.47 | 0.49 | 0.50 | 0.52 | 0.54 | 0.56 | 0.58 | 0.59 | 0.61 | 0.63 | 0.65 |
| | 9 | 0.10 | 0.12 | 0.14 | 0.15 | 0.17 | 0.19 | 0.20 | 0.22 | 0.24 | 0.26 | 0.27 | 0.29 | 0.31 | 0.33 | 0.34 | 0.36 | 0.38 | 0.40 | 0.41 | 0.43 | 0.45 | 0.47 | 0.49 | 0.50 | 0.52 | 0.54 | 0.56 | 0.58 | 0.59 | 0.61 | 0.63 |
| | 10 | 0.08 | 0.10 | 0.12 | 0.14 | 0.15 | 0.17 | 0.19 | 0.21 | 0.22 | 0.24 | 0.26 | 0.27 | 0.29 | 0.31 | 0.33 | 0.34 | 0.36 | 0.38 | 0.40 | 0.42 | 0.43 | 0.45 | 0.47 | 0.49 | 0.50 | 0.52 | 0.54 | 0.56 | 0.58 | 0.59 | 0.61 |
| | 11 | 0.07 | 0.08 | 0.10 | 0.12 | 0.14 | 0.15 | 0.17 | 0.19 | 0.21 | 0.22 | 0.24 | 0.26 | 0.27 | 0.29 | 0.31 | 0.33 | 0.35 | 0.36 | 0.38 | 0.40 | 0.42 | 0.43 | 0.45 | 0.47 | 0.49 | 0.50 | 0.52 | 0.54 | 0.56 | 0.58 | 0.60 |
| | 12 | 0.05 | 0.07 | 0.09 | 0.10 | 0.12 | 0.14 | 0.15 | 0.17 | 0.19 | 0.21 | 0.22 | 0.24 | 0.26 | 0.28 | 0.29 | 0.31 | 0.33 | 0.35 | 0.36 | 0.38 | 0.40 | 0.42 | 0.43 | 0.45 | 0.47 | 0.49 | 0.51 | 0.52 | 0.54 | 0.56 | 0.58 |
| | 13 | 0.03 | 0.05 | 0.07 | 0.09 | 0.10 | 0.12 | 0.14 | 0.15 | 0.17 | 0.19 | 0.21 | 0.22 | 0.24 | 0.26 | 0.28 | 0.29 | 0.31 | 0.33 | 0.35 | 0.36 | 0.38 | 0.40 | 0.42 | 0.43 | 0.45 | 0.47 | 0.49 | 0.51 | 0.52 | 0.54 | 0.56 |
| | 14 | 0.02 | 0.03 | 0.05 | 0.07 | 0.09 | 0.10 | 0.12 | 0.14 | 0.15 | 0.17 | 0.19 | 0.21 | 0.22 | 0.24 | 0.26 | 0.28 | 0.29 | 0.31 | 0.33 | 0.35 | 0.36 | 0.38 | 0.40 | 0.42 | 0.43 | 0.45 | 0.47 | 0.49 | 0.51 | 0.52 | 0.54 |
| | 15 | 0.00 | 0.02 | 0.03 | 0.05 | 0.07 | 0.09 | 0.10 | 0.12 | 0.14 | 0.15 | 0.17 | 0.19 | 0.21 | 0.22 | 0.24 | 0.26 | 0.28 | 0.29 | 0.31 | 0.33 | 0.35 | 0.36 | 0.38 | 0.40 | 0.42 | 0.44 | 0.45 | 0.47 | 0.49 | 0.51 | 0.53 |
| | 16 | | 0.00 | 0.02 | 0.03 | 0.05 | 0.07 | 0.09 | 0.10 | 0.12 | 0.14 | 0.15 | 0.17 | 0.19 | 0.21 | 0.22 | 0.24 | 0.26 | 0.28 | 0.29 | 0.31 | 0.33 | 0.35 | 0.36 | 0.38 | 0.40 | 0.42 | 0.44 | 0.45 | 0.47 | 0.49 | 0.51 |
| | 17 | | | 0.00 | 0.02 | 0.03 | 0.05 | 0.07 | 0.09 | 0.10 | 0.12 | 0.14 | 0.15 | 0.17 | 0.19 | 0.21 | 0.22 | 0.24 | 0.26 | 0.28 | 0.29 | 0.31 | 0.33 | 0.35 | 0.36 | 0.38 | 0.40 | 0.42 | 0.44 | 0.45 | 0.47 | 0.49 |
| | 18 | | | | 0.00 | 0.02 | 0.03 | 0.05 | 0.07 | 0.09 | 0.10 | 0.12 | 0.14 | 0.15 | 0.17 | 0.19 | 0.21 | | | | | | | | | | | | | | | |
| | 19 | | | | | 0.00 | 0.02 | 0.03 | 0.05 | 0.07 | 0.09 | 0.10 | 0.12 | 0.14 | 0.15 | 0.17 | 0.19 | | | | | | | | | | | | | | | |
| | 20 | | | | | | 0.00 | 0.02 | 0.03 | 0.05 | 0.07 | 0.09 | 0.10 | 0.12 | 0.14 | 0.15 | 0.17 | | | | | | | | | | | | | | | |
| | 21 | | | | | | | 0.00 | 0.02 | 0.03 | 0.05 | 0.07 | 0.09 | 0.10 | 0.12 | 0.14 | 0.16 | | | | | | | | | | | | | | | |
| | 22 | | | | | | | | 0.00 | 0.02 | 0.03 | 0.05 | 0.07 | 0.09 | 0.10 | 0.12 | 0.14 | | | | | | | | | | | | | | | |
| | 23 | | | | | | | | | 0.00 | 0.02 | 0.03 | 0.05 | 0.07 | 0.09 | 0.10 | 0.12 | | | | | | | | | | | | | | | |
| | 24 | | | | | | | | | | 0.00 | 0.02 | 0.03 | 0.05 | 0.07 | 0.09 | 0.10 | | | | | | | | | | | | | | | |
| | 25 | | | | | | | | | | | 0.00 | 0.02 | 0.03 | 0.05 | 0.07 | 0.09 | | | | | | | | | | | | | | | |
| | 26 | | | | | | | | | | | | 0.00 | 0.02 | 0.03 | 0.05 | 0.07 | | | | | | | | | | | | | | | |
| | 27 | | | | | | | | | | | | | 0.00 | 0.02 | 0.03 | 0.05 | | | | | | | | | | | | | | | |
| | 28 | | | | | | | | | | | | | | 0.00 | 0.02 | 0.03 | | | | | | | | | | | | | | | |
| | 29 | | | | | | | | | | | | | | | 0.00 | 0.02 | | | | | | | | | | | | | | | |
| | 30 | | | | | | | | | | | | | | | | 0.00 | | | | | | | | | | | | | | | |
| | 31 | | | | | | | | | | | | | | | | | | | | | | | | | | | | | | | |
| | 32 | | | | | | | | | | | | | | | | | | | | | | | | | | | | | | | |
| | 33 | | | | | | | | | | | | | | | | | | | | | | | | | | | | | | | |
| | 34 | | | | | | | | | | | | | | | | | | | | | | | | | | | | | | | |
| | 35 | | | | | | | | | | | | | | | | | | | | | | | | | | | | | | | |
| | 36 | | | | | | | | | | | | | | | | | | | | | | | | | | | | | | | |
| | 37 | | | | | | | | | | | | | | | | | | | | | | | | | | | | | | | |
| | 38 | | | | | | | | | | | | | | | | | | | | | | | | | | | | | | | |
| | 39 | | | | | | | | | | | | | | | | | | | | | | | | | | | | | | | |
| | 40 | | | | | | | | | | | | | | | | | | | | | | | | | | | | | | | |
| | 41 | | | | | | | | | | | | | | | | | | | | | | | | | | | | | | | |
| | 42 | | | | | | | | | | | | | | | | | | | | | | | | | | | | | | | |
| | 43 | | | | | | | | | | | | | | | | | | | | | | | | | | | | | | | |
| | 44 | | | | | | | | | | | | | | | | | | | | | | | | | | | | | | | |
| | 45 | | | | | | | | | | | | | | | | | | | | | | | | | | | | | | | |

TABLE 2-continued

| | | | | | | | | | | | | | | | |
|---|---|---|---|---|---|---|---|---|---|---|---|---|---|---|---|
| 18 | 0.22 | 0.24 | 0.26 | 0.28 | 0.29 | 0.31 | 0.33 | 0.35 | 0.37 | 0.38 | 0.40 | 0.42 | 0.44 | 0.45 | 0.47 |
| 19 | 0.21 | 0.22 | 0.24 | 0.26 | 0.28 | 0.29 | 0.31 | 0.33 | 0.35 | 0.37 | 0.38 | 0.40 | 0.42 | 0.44 | 0.46 |
| 20 | 0.19 | 0.21 | 0.22 | 0.24 | 0.26 | 0.28 | 0.30 | 0.31 | 0.33 | 0.35 | 0.37 | 0.38 | 0.40 | 0.42 | 0.44 |
| 21 | 0.17 | 0.19 | 0.21 | 0.22 | 0.24 | 0.26 | 0.28 | 0.30 | 0.31 | 0.33 | 0.35 | 0.37 | 0.38 | 0.40 | 0.42 |
| 22 | 0.16 | 0.17 | 0.19 | 0.21 | 0.23 | 0.24 | 0.26 | 0.28 | 0.30 | 0.31 | 0.33 | 0.35 | 0.37 | 0.38 | 0.40 |
| 23 | 0.14 | 0.16 | 0.17 | 0.19 | 0.21 | 0.23 | 0.24 | 0.26 | 0.28 | 0.30 | 0.31 | 0.33 | 0.35 | 0.37 | 0.39 |
| 24 | 0.12 | 0.14 | 0.16 | 0.17 | 0.19 | 0.21 | 0.23 | 0.24 | 0.26 | 0.28 | 0.30 | 0.31 | 0.33 | 0.35 | 0.37 |
| 25 | 0.10 | 0.12 | 0.14 | 0.16 | 0.17 | 0.19 | 0.21 | 0.23 | 0.24 | 0.26 | 0.28 | 0.30 | 0.31 | 0.33 | 0.35 |
| 26 | 0.09 | 0.10 | 0.12 | 0.14 | 0.16 | 0.17 | 0.19 | 0.21 | 0.23 | 0.24 | 0.26 | 0.28 | 0.30 | 0.31 | 0.33 |
| 27 | 0.07 | 0.09 | 0.10 | 0.12 | 0.14 | 0.16 | 0.17 | 0.19 | 0.21 | 0.23 | 0.24 | 0.26 | 0.28 | 0.30 | 0.32 |
| 28 | 0.05 | 0.07 | 0.09 | 0.10 | 0.12 | 0.14 | 0.16 | 0.17 | 0.19 | 0.21 | 0.23 | 0.24 | 0.26 | 0.28 | 0.30 |
| 29 | 0.03 | 0.05 | 0.07 | 0.09 | 0.10 | 0.12 | 0.14 | 0.16 | 0.17 | 0.19 | 0.21 | 0.23 | 0.24 | 0.26 | 0.28 |
| 30 | 0.02 | 0.03 | 0.05 | 0.07 | 0.09 | 0.10 | 0.12 | 0.14 | 0.16 | 0.17 | 0.19 | 0.21 | 0.23 | 0.24 | 0.26 |
| 31 | 0.00 | 0.02 | 0.03 | 0.05 | 0.07 | 0.09 | 0.10 | 0.12 | 0.14 | 0.16 | 0.17 | 0.19 | 0.21 | 0.23 | 0.25 |
| 32 | | 0.00 | 0.02 | 0.03 | 0.05 | 0.07 | 0.09 | 0.10 | 0.12 | 0.14 | 0.16 | 0.17 | 0.19 | 0.21 | 0.23 |
| 33 | | | 0.00 | 0.02 | 0.03 | 0.05 | 0.07 | 0.09 | 0.10 | 0.12 | 0.14 | 0.16 | 0.17 | 0.19 | 0.21 |
| 34 | | | | 0.00 | 0.02 | 0.03 | 0.05 | 0.07 | 0.09 | 0.10 | 0.12 | 0.14 | 0.16 | 0.17 | 0.19 |
| 35 | | | | | 0.00 | 0.02 | 0.03 | 0.05 | 0.07 | 0.09 | 0.10 | 0.12 | 0.14 | 0.16 | 0.18 |
| 36 | | | | | | 0.00 | 0.02 | 0.03 | 0.05 | 0.07 | 0.09 | 0.10 | 0.12 | 0.14 | 0.16 |
| 37 | | | | | | | 0.00 | 0.02 | 0.03 | 0.05 | 0.07 | 0.09 | 0.10 | 0.12 | 0.14 |
| 38 | | | | | | | | 0.00 | 0.02 | 0.03 | 0.05 | 0.07 | 0.09 | 0.10 | 0.12 |
| 39 | | | | | | | | | 0.00 | 0.02 | 0.03 | 0.05 | 0.07 | 0.09 | 0.11 |
| 40 | | | | | | | | | | 0.00 | 0.02 | 0.03 | 0.05 | 0.07 | 0.09 |
| 41 | | | | | | | | | | | 0.00 | 0.02 | 0.03 | 0.05 | 0.07 |
| 42 | | | | | | | | | | | | 0.00 | 0.02 | 0.03 | 0.05 |
| 43 | | | | | | | | | | | | | 0.00 | 0.02 | 0.04 |
| 44 | | | | | | | | | | | | | | 0.00 | 0.02 |
| 45 | | | | | | | | | | | | | | | 0.00 |

Under the drying conditions in the concentration range in which the average solid content concentration is 70 wt % or more and 80 wt % or less, the constant drying rate of water is preferably 0.10 kg/(h·m$^2$) or less. Setting the constant drying rate of water under the drying conditions in the concentration range in which the average solid content concentration is 70 wt % or more and 80 wt % or less to 0.10 kg/(h·m$^2$) or less enables to make the drying rate sufficiently slow, and thus the shape of the needle-like protruding portion can be prevented from being deformed by drying.

In addition, there is a case in which wrinkles may be formed on the surface side of the polymer solution (the side opposite to the mold) by drying. These wrinkles are easily formed when the average solid content concentration in the polymer solution in which the surface of the polymer solution loses its fluidity is 60% or more and less than 70%. Setting the drying conditions in the range in which the solid content concentration in the polymer solution is 70 wt % or more and 80 wt % or less as low rate drying conditions enables to reduce wrinkles formed on the surface of the polymer solution, thereby removing the formed wrinkles.

The constant drying rate is a mass of water to be volatilized per unit time and unit area, and its unit is kg/(h·m$^2$). In addition, the constant drying rate Jc can be represented by the following equation.

$$Jc = K_H(Hw - H) = \frac{hc(T - Tw)}{(\Delta hv)w}$$

In addition, each symbol in the equation indicates the following means.

$k_H$: Mass transfer coefficient

Hw: Saturated absolute humidity at wet bulb temperature Tw

H: Absolute humidity of hot air hc: Heat transfer coefficient (for example, assumed that the heat transfer coefficient is 10 kcal/(m$^2$·h·° C.) when the wind speed is set to 0.4 m/s)

T: Hot air temperature (drying temperature)

Tw: Wet bulb temperature (obtained from the conditions for drying humidity and temperature using a psychrometric chart)

$(\Delta hv)w$: evaporation latent heat at wet bulb temperature Tw (obtained from a saturated water vapor table of water)

Further, the value of the heat transfer coefficient according to the type of fluid (affect by the wind speed of dry air) can be estimated to the following degree. However, since the heat transfer coefficient varies depending on the form of flow, physical properties of solid, and the like, the followings are approximate values.

Static air (windless): 4 kcal/(m$^2$·h·° C.)

Flowing air: 10 to 250 kcal/(m$^2$·h·° C.)

Flowing oil: 50 to 1,500 kcal/(m$^2$·h·° C.)

Flowing water: 250 to 5,000 kcal/(m$^2$·h·° C.)

(in terms of SI unit, 1 kcal/(m$^2$·h·° C.)=1.16279 W/m$^2$·h)

Moreover, it is preferable to perform drying at least some of the polymer solution having an average solid content concentration in a range of less than 70 wt % under the condition that the constant drying rate is higher than the constant drying rate in a range in which the solid content concentration is 70 wt % or more and 80 wt % or less. When drying is performed under the condition in which the constant drying rate is high at an average solid content concentration of less than 70 wt %, the drying rate can be increased. In addition, drying of the polymer solution proceeds from the surface of the polymer solution (polymer layer). Accordingly, at an average solid content concentration of less than 70%, the mold side of the polymer layer, that is, the needle-like protruding portion side, is not sufficiently dried and has fluidity. Thus, even when the drying rate is increased, the shape of the tip end of the needle-like protruding portion can be prevented from being deformed.

In addition, since drying of the surface of the polymer solution (polymer layer) proceeds at an average solid content concentration of less than 70%, wrinkles may be formed at a high drying rate. In the embodiment, drying proceeds and the surface is not sufficiently dried in the concentration range in which the average solid content concentration is 70% or more and less than 80%. Thus, wrinkles can be removed by reducing the wrinkles due to a decrease in the drying rate.

Further, since drying sufficiently proceeds and the fluidity of the polymer solution is small in the concentration range in which the average solid content concentration is more than 80 wt %, the polymer layer can be formed without forming wrinkles on the surface of the polymer layer and deforming the shape of the needle-like protruding portion even when the constant drying rate is high.

In order to set the drying condition such that the polymer solution dries slowly, a lid having an opening portion can be placed at a position for covering the polymer solution. FIG. 23 is a view in which a lid 60 is placed on the mold 13. By placing the lid on the mold, a gas vaporized from the polymer solution hardly escapes and the surrounding humidity increases. Accordingly, the drying conditions can be set such that the drying rate is decreased. In addition, control of the humidity by controlling the size of the opening portion 62 enables to control the drying conditions.

Figure 25:
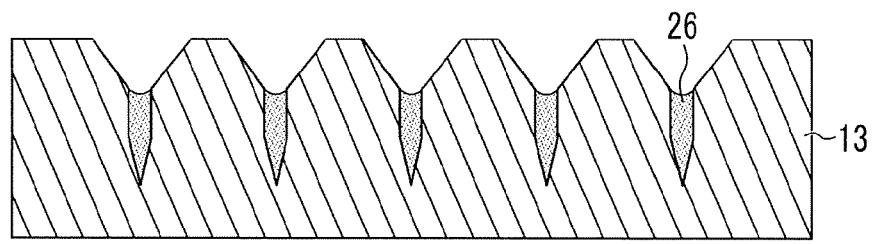
FIG. 25 is a diagram illustrating the other step of forming the polymer sheet.
Figure 26:
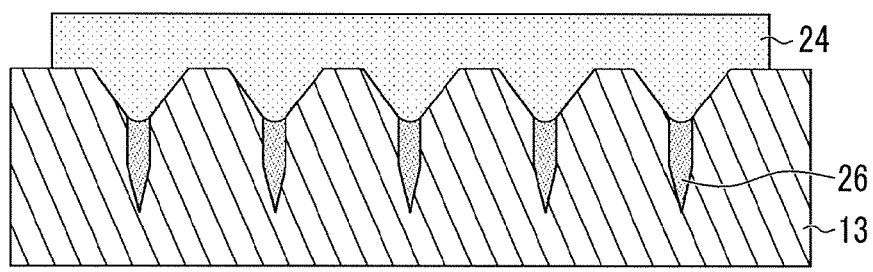
FIG. 26 is a diagram illustrating the other step of forming the polymer sheet.

Next, a second embodiment will be described with reference to FIGS. 24 to 27. As shown in FIG. 24, the needle-like recessed portions 15 of the mold 13 are filled with the drug-containing solution 22. For the filling method, as in the first embodiment, the tip end portion of the nozzle 34 is brought into contact with the mold to fill the needle-like recessed portions with the drug-containing solution. Next, as shown in FIG. 25, the drug-containing solution 22 is dried and solidified to form the drug-containing layer 26 in each of the needle-like recessed portions 15. When the drug-containing solution 22 is dried and solidified, the tip end of the needle-like recessed portion 15 can be filled with the drug-containing solution 22 by the reduced pressure suction from the back surface of the mold 13. Next, as shown in FIG. 26, the polymer solution 24 is applied onto the surface of the drug-containing layer 26 using a dispenser. In addition to the application using the dispenser, for example, a bar coating method, a spin coating method, and an application using a spray or the like can be applied. Since the drug-containing layer 26 is solidified, the drug in the drug-containing layer 26 can be restrained from diffusing to the polymer solution 24.

Figure 27:
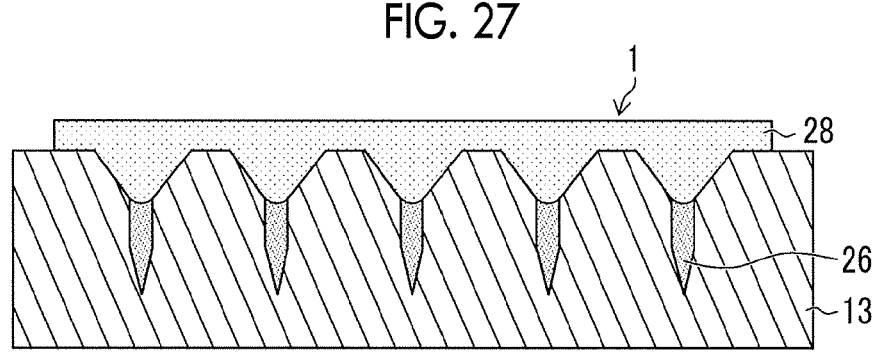
FIG. 27 is a diagram illustrating the other step of forming the polymer sheet.

Next, as shown in FIG. 27, the polymer solution 24 is dried and solidified to form a polymer sheet 1 including the drug-containing layer 26 and a non-drug-containing layer 28.

In the second embodiment, in the step of drying the polymer solution 24, the drying conditions are controlled at the same average solid content concentration as in the first embodiment so that the shape of the polymer layer (transdermal absorption sheet) can be stabilized.

Figure 28:
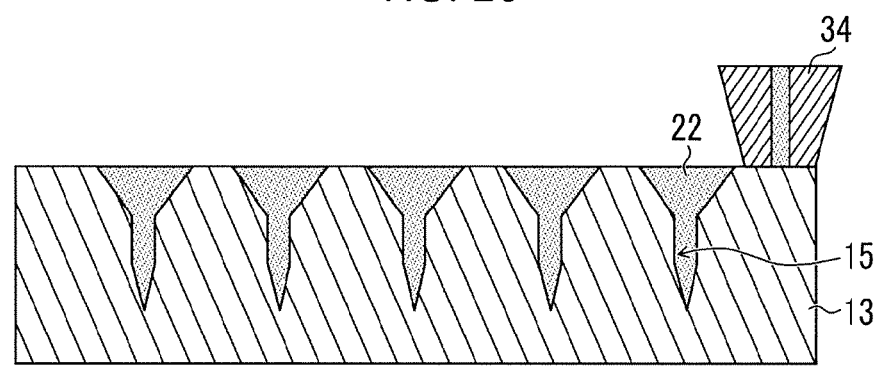
FIG. 28 is a diagram illustrating yet another step of forming a polymer sheet.
Figure 29:
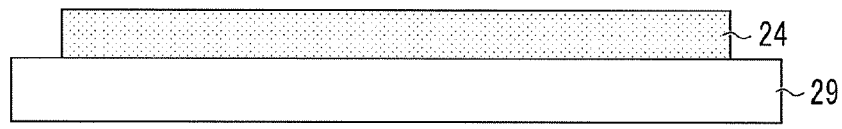
FIG. 29 is a diagram illustrating the other step of forming the polymer sheet.
Figure 30:
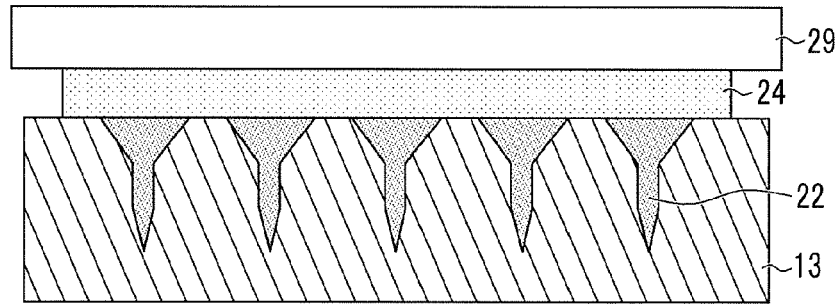
FIG. 30 is a diagram illustrating the other step of forming the polymer sheet.
Figure 31:
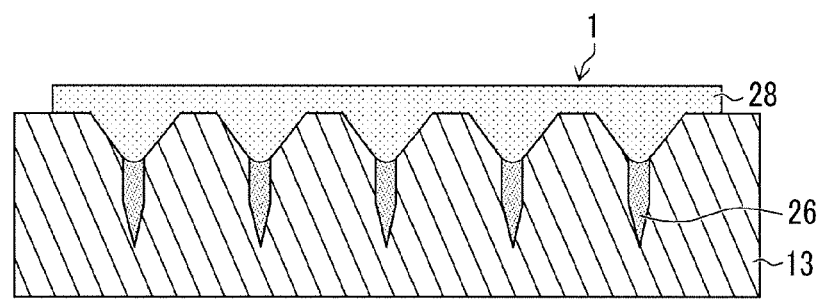
FIG. 31 is a diagram illustrating the other step of forming the polymer sheet.

Next, a third embodiment will be described with reference to FIGS. 28 to 31. As shown in FIG. 28, the needle-like recessed portions 15 of the mold 13 are filled with the drug-containing solution 22. For the filling method, as in the first and second embodiments, the tip end portion of the nozzle is brought into contact with the mold to fill the needle-like recessed portions with the drug-containing solution. Next, as shown in FIG. 29, the polymer solution 24 is applied onto another support 29. The support 29 is not limited, but for example, polyethylene, polyethylene terephtalate, polycarbonate, polypropylene, an acrylic resin, triacetylcellulose, or the like may be used. Next, as shown in FIG. 30, the polymer solution 24 formed on the support 29 is laid on the mold 13 with the needle-like recessed portions 15 filled with the drug-containing solution 22. Next, as shown in FIG. 31, the drug-containing solution 22 and the polymer solution 24 are dried and solidified to form the polymer sheet 1 including the drug-containing layer 26 and the non-drug-containing layer 28.

In the third embodiment, in the step of drying the polymer solution, the drying conditions are controlled at the same average solid content concentration as in the first and second embodiments, and the shape of the polymer layer (transdermal absorption sheet) can be stabilized.

In the first to third embodiments, the drug-containing solution and the polymer solution are separately prepared and separately applied to the mold to form the transdermal absorption sheet. However, a polymer layer (transdermal absorption sheet) can be produced using one type of polymer solution by preparing a drug-containing polymer solution. In this case, the shape of the polymer layer (transdermal absorption sheet) can be stabilized by setting the same conditions as in the first embodiment in the concentration range of the average solid content concentration of one type of polymer solution.

Figure 32:
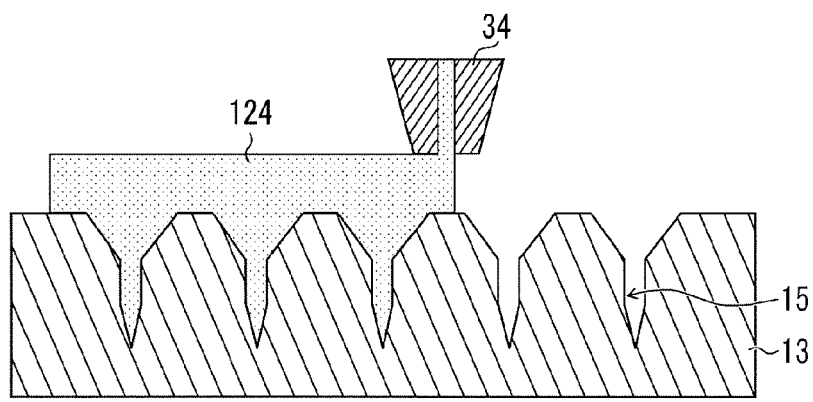
FIG. 32 is a diagram illustrating a step of forming a polymer sheet using one type of polymer solution.
Figure 33:
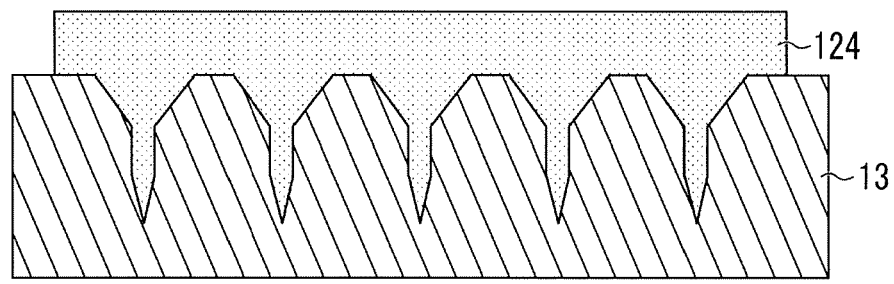
FIG. 33 is a diagram illustrating the step of forming the polymer sheet using one type of polymer solution.
Figure 34:
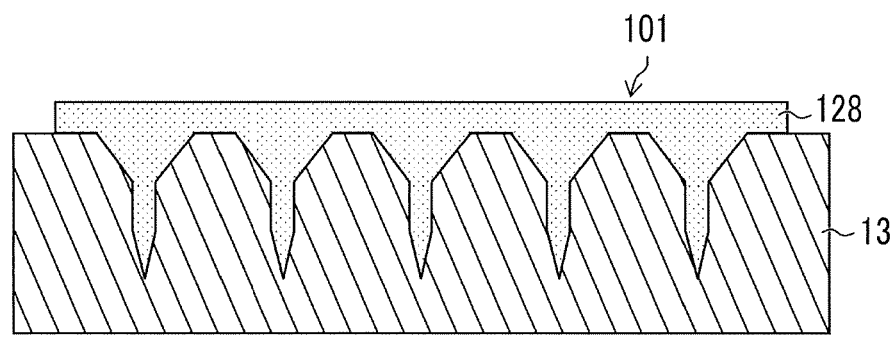
FIG. 34 is a diagram illustrating the step of forming the polymer sheet using one type of polymer solution.

FIGS. 32 to 34 are diagrams illustrating a step of forming a polymer sheet 101 using one type of polymer solution 124. As shown in FIG. 32, the needle-like recessed portions 15 of the mold 13 are filled with the polymer solution 124 containing a drug. Filling of the polymer solution 124 can be performed using the nozzle 34. In addition, instead of using the nozzle 34, an application using a dispenser, a bar coating method, a spin coating method, and an application using a spray or the like can be applied. It is preferable that the tip end of the needle-like recessed portion 15 is filled with the polymer solution by the reduced pressure suction from the back surface of the mold 13. FIG. 33 is a diagram showing a state after the mold 13 is filled with the polymer solution 124.

Next, as shown in FIG. 34, the polymer solution 124 is dried and solidified and the polymer sheet 101 including the drug-containing polymer layer 128 is formed.

After the polymer sheets 1 and 101 in which the needle-like protruding portions are formed on the surface are formed, the process proceeds to a step of peeling off the polymer sheets 1 and 101 from the mold 13. A peeling-off step of peeling off the polymer sheet 1 will be described below, but peeling-off of the polymer sheet 101 can be performed in the same manner.

Figure 35:
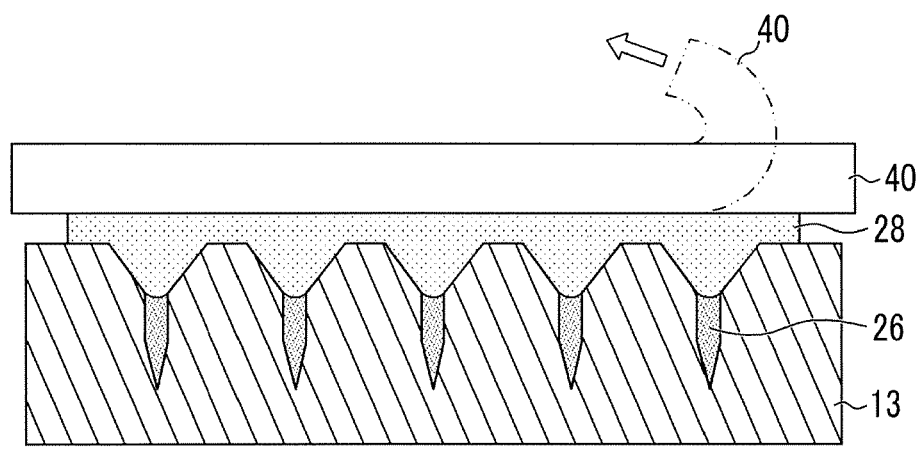
FIG. 35 is a diagram illustrating a peeling-off step.
Figure 36:
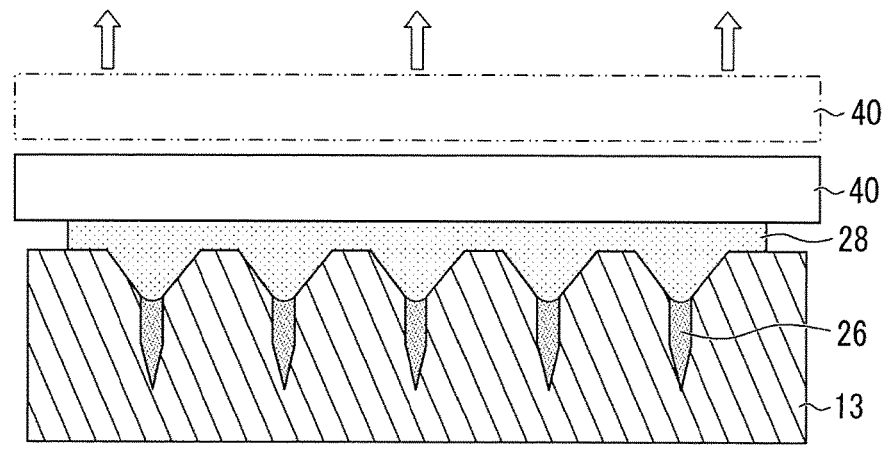
FIG. 36 is a diagram illustrating another peeling-off step.

A method of peeling off the polymer sheet 1 from the mold 13 is not particularly limited. At the time of peeling-off, the needle-like protruding portions are desirably prevented from being bent or broken. Specifically, as shown in FIG. 35, a sheet-like base material 40 on which a pressure sensitive adhesive layer having adhesiveness is formed is attached onto the polymer sheet 1, and then the polymer sheet 1 can be peeled off by turning the base material 40 over at the end portion of the polymer sheet. However, this method may cause the needle-like protruding portions to be bent. Therefore, as shown in FIG. 36, a method may be applied in which suckers (not shown) of the polymer sheet 1 are installed on the base material 40 and the base material 40 is then sucked using air and lifted perpendicularly.

Normally, in the case in which a structure with needle-like protruding portions with a high aspect ratio is peeled off from the mold 13, high stress is applied due to a large contact area. The microneedles that are needle-like protruding portions may be destroyed and remain in the needle-like recessed portions 15 instead of being peeled off from the mold 13, and a transdermal absorption sheet to be prepared may be defective. Thus, the mold 13 is preferably constituted of a material that is very easily peelable. Furthermore, since the mold 13 constituted of a highly elastic soft material allows relaxation of stress applied to the needle-like protruding portions at the time of peeling-off, it is preferable that mold is constituted of a highly elastic soft material.

Normally, as in the embodiment, in the case in which a structure with needle-like protruding portions having a high aspect ratio is peeled off from the mold 13, high stress is applied due to a large contact area. The microneedles that are needle-like protruding portions may be destroyed and remain in the needle-like recessed portions 15 instead of being peeled off from the mold 13, and a transdermal absorption sheet to be prepared may be defective. Thus, in the embodiment, the mold 13 is preferably constituted of a material that is very easily peelable. Furthermore, the mold 13 constituted of a highly elastic soft material allows relaxation of stress applied to the needle-like protruding portions at the time of peeling-off.

Figure 37:
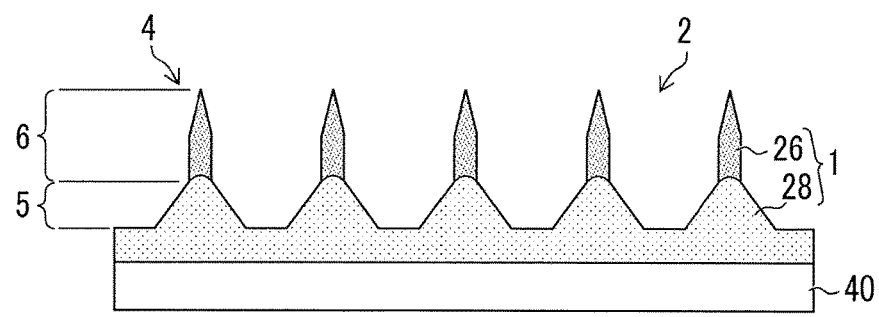
FIG. 37 is a cross-sectional view showing a transdermal absorption sheet.

FIG. 37 shows a transdermal absorption sheet 2 constituted of the polymer sheet 1 peeled off from the mold 13. The transdermal absorption sheet 2 is constituted of the base material 40, the drug-containing layer 26 formed on the base material 40, and the layer 28 not substantially containing the drug. Needle-like protruding portions 4 on the transdermal absorption sheet 2 are each constituted of a truncated cone portion 5 and a needle portion 6 on the truncated cone portion 5. The needle portion 6 mainly has a conical or pyramidal needle portion and a cylindrical or rectangular columnar body portion. However, the needle-like protruding portions 4 are not limited to this shape.

Further, a sheet portion average thickness which is the average thickness of the non-drug-containing layer 28 excluding the truncated cone portion 5 is preferably 50 μm or more and 500 μm or less. The sheet portion average thickness can be obtained by cutting the polymer sheet after peeling-off into arbitrarily cross-sectional surfaces and measuring the thickness by observing the cross-sectional surfaces with a microscope or the like.

EXAMPLES

Hereinafter, the present invention is further specifically described using examples of the present invention. Materials, usages, rates, the contents of treatments, the treatment procedures, and the like illustrated in the following examples may be appropriately changed unless the change departs from the spirits of the present invention. Thus, the scope of the present invention should not be interpreted in a limited manner based on the specific examples illustrated below.

EXAMPLES (Preparation of Mold)

Figure 38:
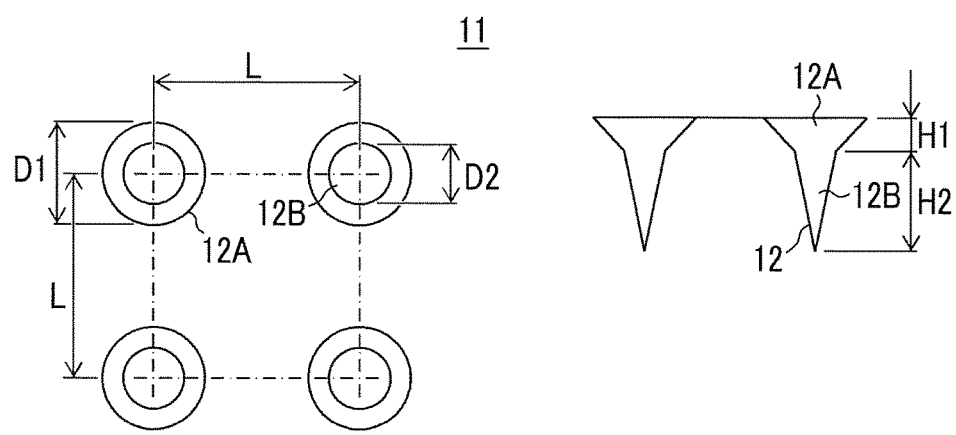
FIG. 38 is a plan view and a side view showing an original plate.

The original plate 11 as shown in FIG. 38 was produced by grinding a surface of a smooth ALMIGO plate having one side of 40 mm so as to form shape portions 12 each with a needle-like structure that are arranged at a pitch L of 1,000 μm in a two-dimensional array with 10 columns and 10 rows. Each shape portions 12 with a needle-like structure includes: a truncated cone 12A with a bottom surface diameter D1 of 500 μm and a height H1 of 150 μm; and a cone 12B formed on the truncated cone 12A and having a diameter D2 of 300 μm and a height H2 of 500 μm.

A film was formed on the original plate 11 to have a thickness of 0.700 mm using silicone rubber (SILASTIC-MDX4-4210, manufactured by Dow Corning Toray Co., Ltd.), thermally cured, and peeled-off. Thus, an inverted article made of silicone rubber was prepared. The inverted article made of silicone rubber was trimmed so as to leave a planar portion with one side of 30 mm on whose central portion needle-like recessed portions were formed to be two-dimensionally arranged in 10 columns and 10 rows, and the obtained portion was used as a mold. A surface of the mold corresponding to the exposed opening portion of each of the needle-like recessed portions was the surface of the mold.

(Preparation of the Drug-Containing Solution)

Hydroxyethyl starch (manufactured by Fresenius Kabi) was dissolved into water to prepare a 4 wt % aqueous solution in terms of weight percent. As a drug, 1 wt % human serum albumin (manufactured by Wako Pure Chemical Industries, Ltd.) was added to the solution to obtain the drug-containing solution. After the solution was prepared, the solution was exposed for 4 minutes under a reduced pressure environment of 3 kPa and deaeration was performed.

(Preparation of Polymer Solution as Base Material)

(1) Sodium chondroitin sulfate (manufactured by Maruha Nichiro Corporation) was dissolved into water to prepare a 40 wt % aqueous solution in terms of weight percent. After the solution was prepared, the solution was exposed for 4 minutes under a reduced pressure environment of 3 kPa and deaeration was performed.

(2) Hydroxypropyl cellulose (manufactured by Nippon Soda Co., Ltd.) was dissolved into water to prepare a 30 wt % aqueous solution in terms of weight percent. After the solution was prepared, the solution was exposed for 4 minutes under a reduced pressure environment of 3 kPa and deaeration was performed.

(3) DEXTRAN 70 (manufactured by Meito Sangyo Co., Ltd.) was dissolved into water to prepare a 40 wt % aqueous solution in terms of weight percent. After the solution was prepared, the solution was exposed for 4 minutes under a reduced pressure environment of 3 kPa and deaeration was performed.

(Drug Solution Filling Step and Drug Solution Drying Step)

A drug solution filling apparatus includes a driving unit which has an X axis driving portion and a Z axis driving portion and controls relative position coordinates of a mold and a nozzle, a liquid feeding apparatus (Super small amount fixed-quantity dispenser SMP-III, manufactured by Musashi Engineering, Inc.) from which the nozzle is detachable, a suction base which fixes the mold, a laser displacement meter (HL-C201A, manufactured by Panasonic Corporation) which measures the shape of the mold surface, a load cell which measures nozzle pressing pressure (LCX-A-500N, manufactured by Kyowa Electronic Instruments Co., Ltd.), and a control system which controls the Z axis based on the surface shape and the data of the value of measured pressing pressure.

The mold was placed such that the surface is laid on the horizontal suction base. The pressure was reduced in the direction of the mold back surface with a suction pressure of a gauge pressure of 90 kPa to fix the mold onto the suction base.

A stainless steel nozzle having a shape shown in FIG. 15 was prepared and a slit-like opening portion with a length of 12 mm and a width of 0.2 mm was formed at the center of a lip portion with a length of 20 mm and a width of 3 mm. The nozzle was attached to a drug solution tank. The inside of the drug solution tank and the nozzle was filled with the drug-containing solution of 3 mL. The nozzle was adjusted in order for the opening portion to be parallel to the first column constituted of a plurality of needle-like recessed portions formed in the surface of the mold. The nozzle was pressed against the mold with a pressure (pressing pressure) of 0.144 kgf/cm$^2$ (1.4 N/cm$^2$) at the position with a distance of 2 mm from the first column in a direction opposite to the second column. While the nozzle was moved in a direction perpendicular to the length direction of the opening portion at 1 mm/sec in a state in which the nozzle was kept pressed against the mold, and the Z axis was controlled such that the variation in pressing pressure is in a range of ±0.05 kgf/cm$^2$ (0.49 N/cm$^2$), the drug-containing solution was discharged using the liquid feeding apparatus through the opening portion at 0.31 μL/sec for 10 seconds. Movement of the nozzle was stopped at the position with a distance of 2 mm from the tenth column of the plurality of two-dimensionally arranged needle-like recessed portions in a direction opposite to the ninth column. The nozzle was then separated from the mold.

The drug solution filling the needle-like recessed portions of the mold was dried and the drug was localized at the tip end.

(Polymer Solution Filling Step and Polymer Solution Drying Step)

The mold in which the drug solution was dried was sucked and fixed by the suction apparatus. The silicone rubber die frame having an opening portion having a diameter of 16 mm and having a thickness of 0.5 mm was installed such that the needle-like recessed portion region of the mold is positioned at the center. In a state in which the back surface of the mold was sucked, about 100 mg of a polymer solution which becomes a base material was applied to the inside of the opening portion of the mold frame to fill the needle-like recessed portions with the polymer solution.

After the filling, the solution was dried under the drying conditions shown in Table 3 below.

(Peeling-Off Step)

The polymer layer was peeled off from the mold by turning the polymer layer over at the end portion to produce a transdermal absorption sheet having needle-like protruding portions arranged two-dimensionally, in which human serum albumin is localized at the tip end.

(Shape of Transdermal Absorption Sheet) <Evaluation>
[Wrinkles]

The surface shape of the back surface side of the transdermal absorption sheet on which the needle-like protruding portions are not present was measured with a probe type step profiler to evaluate whether wrinkles are formed or not. The surface shape of the back surface was obtained in various scanning directions and a stripe-like uneven shape having a step of 10 μm or more with respect to a reference surface was determined as a wrinkle.

[Shape of Needle-Like Protruding Portion]

The shape of the needle-like protruding portion was observed with a microscope to evaluate the quality of the shape.

TABLE 3

| Average solid content concentration of polymer solution | Upper part: Drying condition Lower part: Constant drying rate | | | Wrinkle | Needle-like protruding portion shape |
|---|---|---|---|---|---|
| | <70 wt % | 70 wt % or more and 80 wt % or less | >80 wt % | | |
| Example 1 | 23° C., 35% RH Wind speed: 0.4 m/s 0.15 kg/(h · m$^2$) | 30° C., 61% RH Wind speed: 0.4 m/s 0.10 kg/(h · m$^2$) | 30° C., 61% RH Wind speed: 0.4 m/s 0.10 kg/(h · m$^2$) | Not formed | Good |
| Example 2 | 30° C., 61% RH Wind speed: 0.4 m/s 0.10 kg/(h · m$^2$) | 30° C., 61% RH Wind speed: 0.4 m/s 0.10 kg/(h · m$^2$) | 44° C., 4% RH Wind speed: 0.4 m/s 0.45 kg/(h · m$^2$) | Not formed | Good |
| Example 3 | 23° C., 35% RH Wind speed: 0.4 m/s 0.15 kg/(h · m$^2$) | 30° C., 61% RH Wind speed: 0.4 m/ 0.10 kg/(h · m$^2$) | 44° C., 4% RH Wind speed: 0.4 m/s 0.45 kg/(h · m$^2$) | Not formed | Good |
| Comparative Example 1 | 23° C., 35% RH Wind speed: 0.4 m/s 0.15 kg/(h · m$^2$) | 23° C., 35% RH Wind speed: 0.4 m/s 0.15 kg/(h · m$^2$) | 44° C., 4% RH Wind speed: 0.4 m/s 0.45 kg/(h · m$^2$) | Formed | Poor |
| Comparative Example 2 | 23° C., 35% RH Wind speed: 0.4 m/s 0.15 kg/(h · m$^2$) | 44° C., 4% RH Wind speed: 0.4 m/s 0.45 kg/(h · m$^2$) | 44° C., 4% RH Wind speed: 0.4 m/s 0.45 kg/(h · m$^2$) | Formed | Poor |
| Comparative Example 3 | 15° C., 30% RH Wind speed: 4.0 m/s 0.14 kg/(h · m$^2$) or more | 15° C., 30% RH Wind speed: 4.0 m/s 0.14 kg/(h · m$^2$) or more | 15° C., 30% RH Wind speed: 4.0 m/s 0.14 kg/(h · m$^2$) or more | Formed | Poor |

The constant drying rate of water obtained from Tables 1 and 2 above was 0.15 kg/(h·m$^2$) at 23° C. and 35% RH, 0.10 kg/(h·m$^2$) at 30° C. and 61% RH, and 0.45 kg/(h·m$^2$) at 44° C. and 4% RH.

As shown in Examples 1 to 3, the drying condition in which the solid content concentration of the polymer solution is 70 wt % or more and 80 wt % or less was set as a condition in which the constant drying rate is low and thus a transdermal absorption sheet in which wrinkles are not formed and the shape of the needle-like protruding portion is good could be produced.

The condition of Comparative Example 3 is an example in which drying is performed under the condition in which the drying rate is lowest among the drying conditions in JP2008-245955A exemplified as a document of related art. Since the wind speed is different in Comparative example 3, conversion from Table 2 cannot be made. However, the wind speed is high and thus it is considered that the drying rate is 0.14 kg/(h·m$^2$) or more. Even when drying is performed under the condition in which the drying rate is lowest among the conditions described in JP2008-245955A, wrinkles are formed and the shape of the needle-like protruding portion is poor. It is confirmed that under the drying conditions of JP2008-245955A, a transdermal absorption sheet having a good shape cannot be produced and the drying conditions of JP2008-245955A are not sufficient.

EXPLANATION OF REFERENCES 1, 101: Polymer sheet
2: Transdermal absorption sheet
4: Needle-like protruding portion
5: Truncated cone portion
6: Needle portion
10: Microneedle
10A: Ridge line
10B: Microneedle tip end
10C: Quadrangular pyramidal surface
11: Original plate
12: Shape portion
12A: Truncated cone
12B: Cone
13: Mold
14: Frame
15: Needle-like recessed portion
15A: Inlet portion
15B: Intermediate recessed portion
15C: Tip end recessed portion
15D: Air vent hole
18: Mold complex
19: Gas permeable sheet
20: Base
22: Drug-containing solution
24, 124: Polymer solution
26: Drug-containing layer
28: Non-drug-containing layer (Polymer layer)
29: Support
30: Tank
32: Pipe
34, 134: Nozzle
34A: Lip portion
34B: Opening portion
36, 136: Liquid feeding apparatus
40: base material
60: Lid
62: Opening portion
128: Drug-containing polymer solution

What is claimed is:

1. A method of producing a transdermal absorption sheet comprising, in this order:
   a polymer solution filling step of filling needle-like recessed portions on a mold having the needle-like recessed portions arranged two-dimensionally with a polymer solution;
   a polymer solution drying step of drying the polymer solution filling the needle-like recessed portions to form a polymer layer; and
   a peeling-off step of peeling off the polymer layer from the mold,
   wherein in the polymer solution drying step, low rate drying conditions are set in a concentration range in which an average solid content concentration of the polymer solution is 70 wt % or more and 80 wt % or less in terms of weight percent, and
   when a constant drying rate of water is used as an index, in the concentration range in which the average solid content concentration of the polymer solution is 70 wt % or more and 80 wt % or less in terms of weight percent, the constant drying rate is set to be lower than a maximum value of a constant drying rate under drying conditions in a concentration range in which the average solid content concentration of the polymer solution is less than 70 wt % and also set to be lower than a maximum value of a constant drying rate under drying conditions in a concentration range in which the average solid content concentration of the polymer solution is more than 80 wt % in terms of weight percent, and
   wherein the constant drying rate of water under the low rate drying conditions in the concentration range in which the average solid content concentration of the polymer solution is 70 wt % or more and 80 wt % or less in terms of weight percent is 0.10 kg/(h·m$^2$) or less.

2. The method of producing a transdermal absorption sheet according to claim 1,
   wherein in the concentration range in which the average solid content concentration of the polymer solution is 70 wt % or more and 80 wt % or less in terms of weight percent, a lid having an opening portion is placed at a position where the lid covers the polymer solution.

3. The method of producing a transdermal absorption sheet according to claim 1, further comprising
   a drug solution filling step of filling the needle-like recessed portions with a drug-containing solution before the polymer solution filling step.

4. The method of producing a transdermal absorption sheet according to claim 3, further comprising
   a drug solution drying step of drying the drug-containing solution after the drug solution filling step before the polymer solution filling step.

5. The method of producing a transdermal absorption sheet according to claim 1,
   wherein the polymer solution contains a drug.

6. The method of producing a transdermal absorption sheet according to claim 1,
   wherein the constant drying rate in at least part of the concentration range in which the average solid content concentration of the polymer solution is less than 70 wt % in terms of weight percent is set to be higher than the constant drying rate in the concentration range in which the average solid content concentration of the polymer solution is 70 wt % or more and 80 wt % or less in terms of weight percent.

7. The method of producing a transdermal absorption sheet according to claim 1,
   wherein the constant drying rate in at least part of the concentration range in which the average solid content concentration of the polymer solution is more than 80 wt % in terms of weight percent is set to be higher than the constant drying rate in the concentration range in which the average solid content concentration of the polymer solution is 70 wt % or more and 80 wt % or less in terms of weight percent.

8. The method of producing a transdermal absorption sheet according to claim 1,
   wherein a polymer contained in the polymer solution includes at least one of sodium chondroitin sulfate, hydroxypropyl cellulose, or dextran.

9. The method of producing a transdermal absorption sheet according to claim 1,
   wherein a sheet portion average thickness after the polymer solution drying step is 50 μm or more and 500 μm or less.

* * * * *